United States Patent [19]
Cantu et al.

[11] Patent Number: 6,027,441
[45] Date of Patent: Feb. 22, 2000

[54] SYSTEMS AND METHODS PROVIDING A LIQUID-PRIMED, SINGLE FLOW ACCESS CHAMBER

[75] Inventors: Robert J Cantu, Lake In The Hills; Kyungyoon Min, Gurnee; Douglas W Reitz, Green Oaks, all of Ill.

[73] Assignee: Baxter International Inc., Deerfield, Ill.

[21] Appl. No.: 08/886,179

[22] Filed: Jul. 1, 1997

[51] Int. Cl.[7] .............................. B04B 11/00; B04B 11/04
[52] U.S. Cl. ........................ 494/37; 210/143; 210/218; 210/416.1; 210/739; 210/782; 494/5
[58] Field of Search ................... 210/718, 739, 210/767, 97, 143, 218, 416.1, 782; 494/23, 5, 27, 37

[56] References Cited

U.S. PATENT DOCUMENTS

| | | |
|---|---|---|
| 3,297,244 | 1/1967 | Hein . |
| 3,456,875 | 7/1969 | Hein . |
| 3,737,096 | 6/1973 | Jones et al. . |
| 3,987,961 | 10/1976 | Sinn et al. . |
| 4,285,464 | 8/1981 | Latham Jr. . |
| 4,405,079 | 9/1983 | Schoendorfer .............................. 494/1 |
| 4,445,883 | 5/1984 | Schroendorfer .......................... 494/21 |
| 4,447,220 | 5/1984 | Eberle ........................................ 494/26 |
| 4,767,397 | 8/1988 | Hohenberg et al. ....................... 494/85 |
| 4,923,612 | 5/1990 | Trivett et al. ........................... 210/646 |
| 4,990,132 | 2/1991 | Unger et al. ................................. 604/6 |
| 5,114,396 | 5/1992 | Unger et al. ............................... 494/37 |
| 5,269,924 | 12/1993 | Rochat ...................................... 210/445 |
| 5,316,667 | 5/1994 | Brown et al. ............................... 210/85 |
| 5,356,365 | 10/1994 | Brierton .................................... 494/14 |
| 5,360,542 | 11/1994 | Williamson, IV et al. ............. 210/232 |
| 5,368,542 | 11/1994 | McMannis et al. ....................... 494/45 |
| 5,549,458 | 8/1996 | Chapman et al. ....................... 417/360 |
| 5,551,942 | 9/1996 | Brown et al. .............................. 494/45 |
| 5,573,678 | 11/1996 | Brown et al. ............................. 210/782 |
| 5,651,766 | 7/1997 | Kingsley et al. ........................... 604/6 |
| 5,690,815 | 11/1997 | Krasnoff et al. .......................... 210/97 |
| 5,733,253 | 3/1998 | Headley et al. ............................. 604/4 |

*Primary Examiner*—John Kim
*Attorney, Agent, or Firm*—Bradford R.L. Price; Denise M. Serewicz; Daniel D. Ryan

[57] ABSTRACT

Blood processing systems and methods rotate a processing chamber on a rotating element. The processing chamber includes a first compartment and a second compartment. Blood is conveyed into the first compartment for centrifugal separation into components. A liquid free of blood occupies the second compartment to counter-balance the first compartment during rotation on the rotating element. In one embodiment, the second compartment is served by a single fluid flow access. Prior to use, the single access is coupled to tubing, through which a vacuum is drawn to remove air from the second compartment. While the vacuum exists, communication is opened between the tubing and a source of liquid. The vacuum draws the liquid into the second compartment through the single access, thereby priming the second compartment for use.

4 Claims, 28 Drawing Sheets

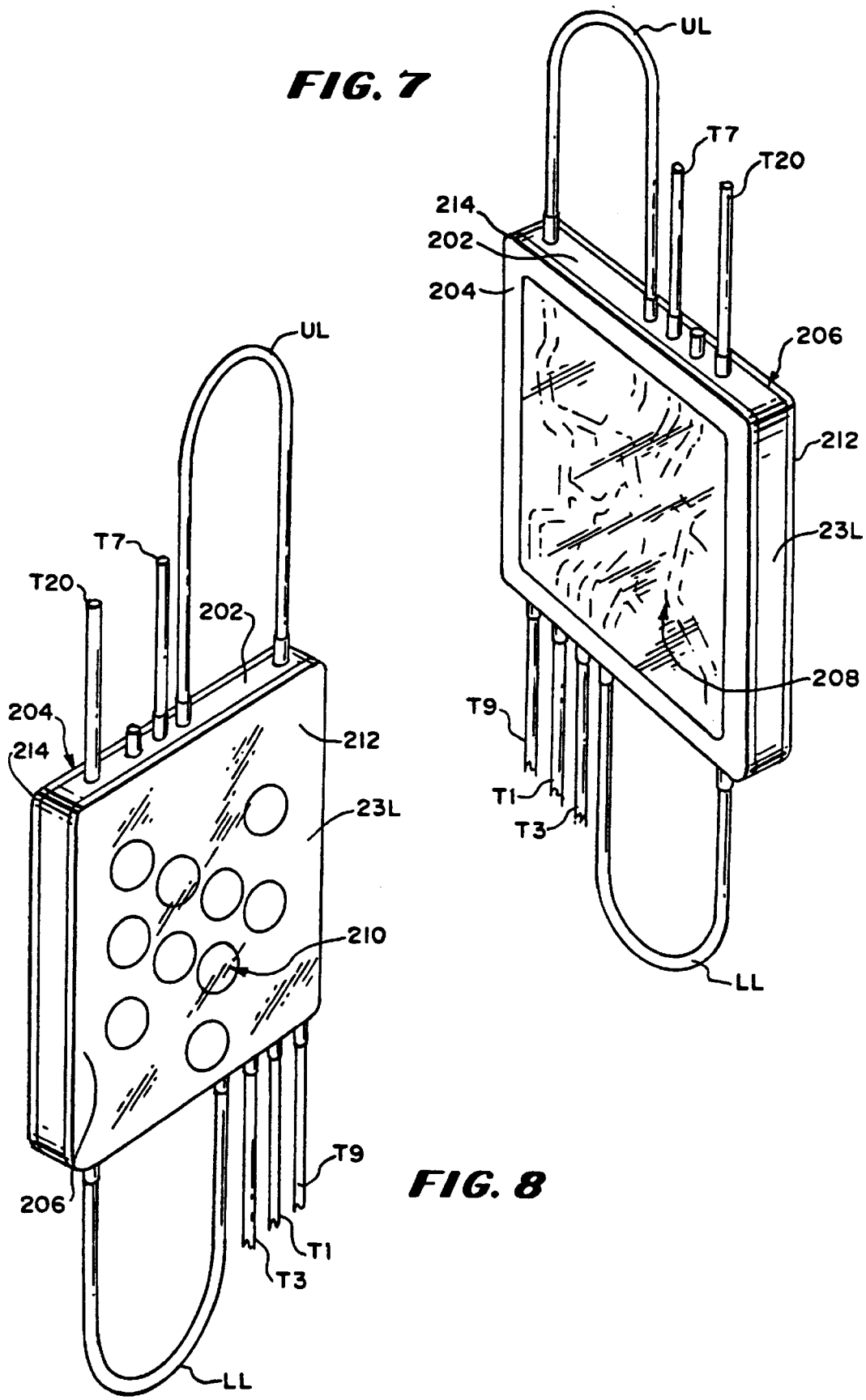

SYSTEMS AND METHODS PROVIDING A LIQUID-PRIMED, SINGLE FLOW ACCESS CHAMBER

FIELD OF THE INVENTION

The invention relates to centrifugal processing systems and apparatus.

BACKGROUND OF THE INVENTION

Today blood collection organizations routinely separate whole blood by centrifugation into its various therapeutic components, such as red blood cells, platelets, and plasma.

Conventional blood processing systems and methods use durable centrifuge equipment in association with single use, sterile processing chambers, typically made of plastic. The centrifuge equipment introduces whole blood into these chambers while rotating them to create a centrifugal field.

Whole blood separates within the rotating chamber under the influence of the centrifugal field into higher density red blood cells and platelet-rich plasma. An intermediate layer of leukocytes forms the interface between the red blood cells and platelet-rich plasma.

SUMMARY OF THE INVENTION

One aspect of the invention provides blood processing systems and methods comprising a processing chamber carried on a rotating element. The processing chamber includes a first compartment containing blood for centrifugal separation into components. The processing chamber also includes a second compartment containing a liquid free of blood. The liquid in the second compartment counterbalances the first compartment during rotation on the rotating element.

In a preferred embodiment, the second compartment is substantially free of air, and the liquid in the second compartment is subject to a positive pressure.

In one embodiment, the second compartment has a single access, e.g., a single access port or multiple ports served by a single access path, such that two way fluid flow simulateneously into and out of the compartment is not possible. Another aspect of the invention provides systems and methods to prime the single access compartment, or any like chamber serviced by a single access. The systems and methods operate a pump element to draw a vacuum in the chamber through the single access. While the vacuum exists, the systems and methods open communication between the chamber and a source of liquid. The vacuum draws the liquid into the chamber through the single access to prime the chamber.

In a preferred embodiment, the systems and methods command a pump element to convey the liquid into the chamber while the vacuum also draws the liquid into the chamber. A positive pressure condition is thereby established in the primed chamber.

Other features and advantages of the invention will become apparent upon reviewing the following specification, drawings, and appended claims.

BRIEF DESCRIPTION OF THE DRAWINGS

FIG. 7 is a perspective view of the back side of a cassette that forms a part of the fluid circuit shown in FIG. 6;

FIG. 8 is a perspective view of the front side of the cassette shown in FIG. 7;

Figure 6:
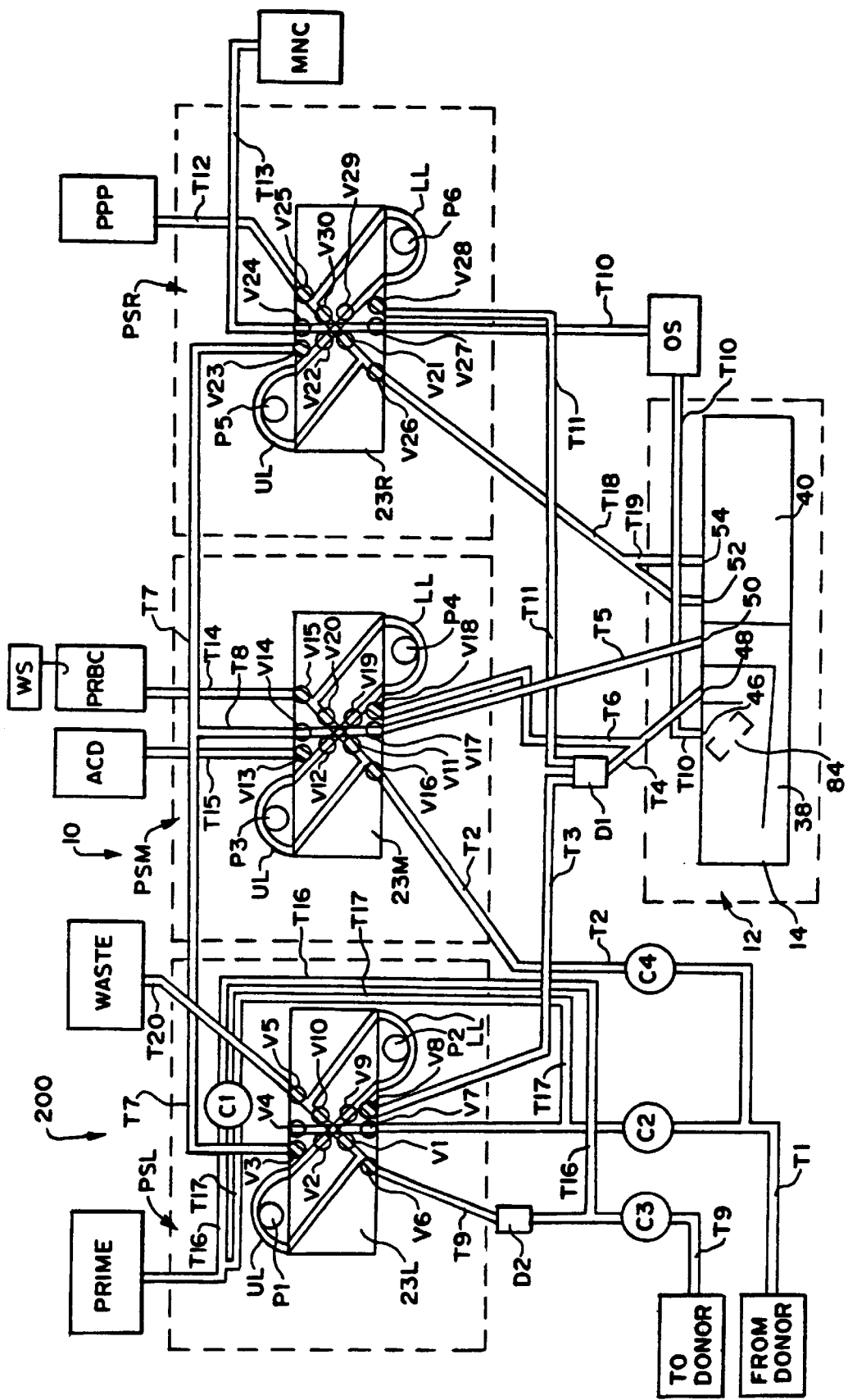
FIG. 6 is a schematic view of the fluid circuit shown in FIG. 5.
Figure 20:
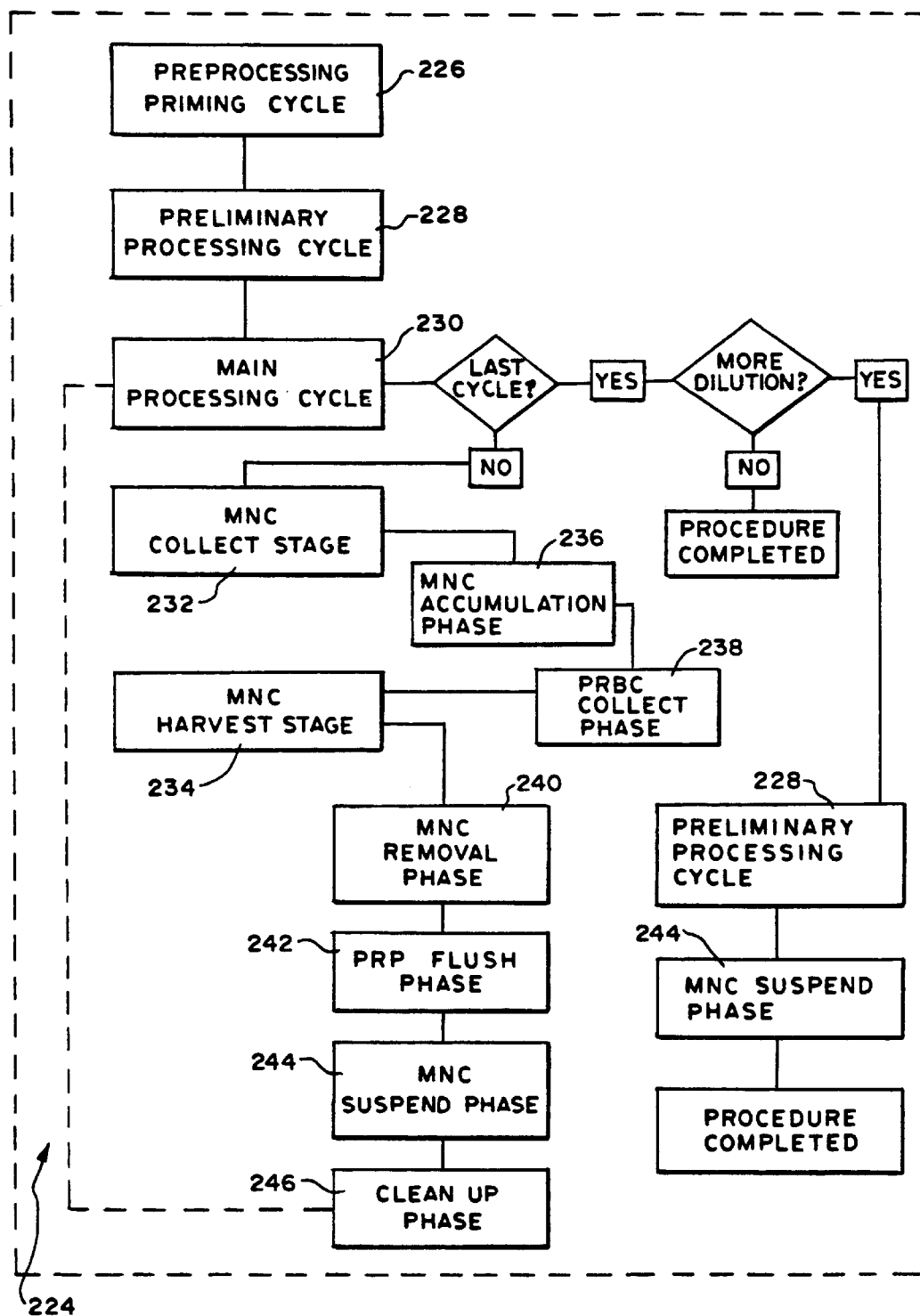
FIG. 20 is a flow chart showing the various cycles and phases of the MNC collection procedure that the controller shown in FIG. 19 governs.
Figure 23:
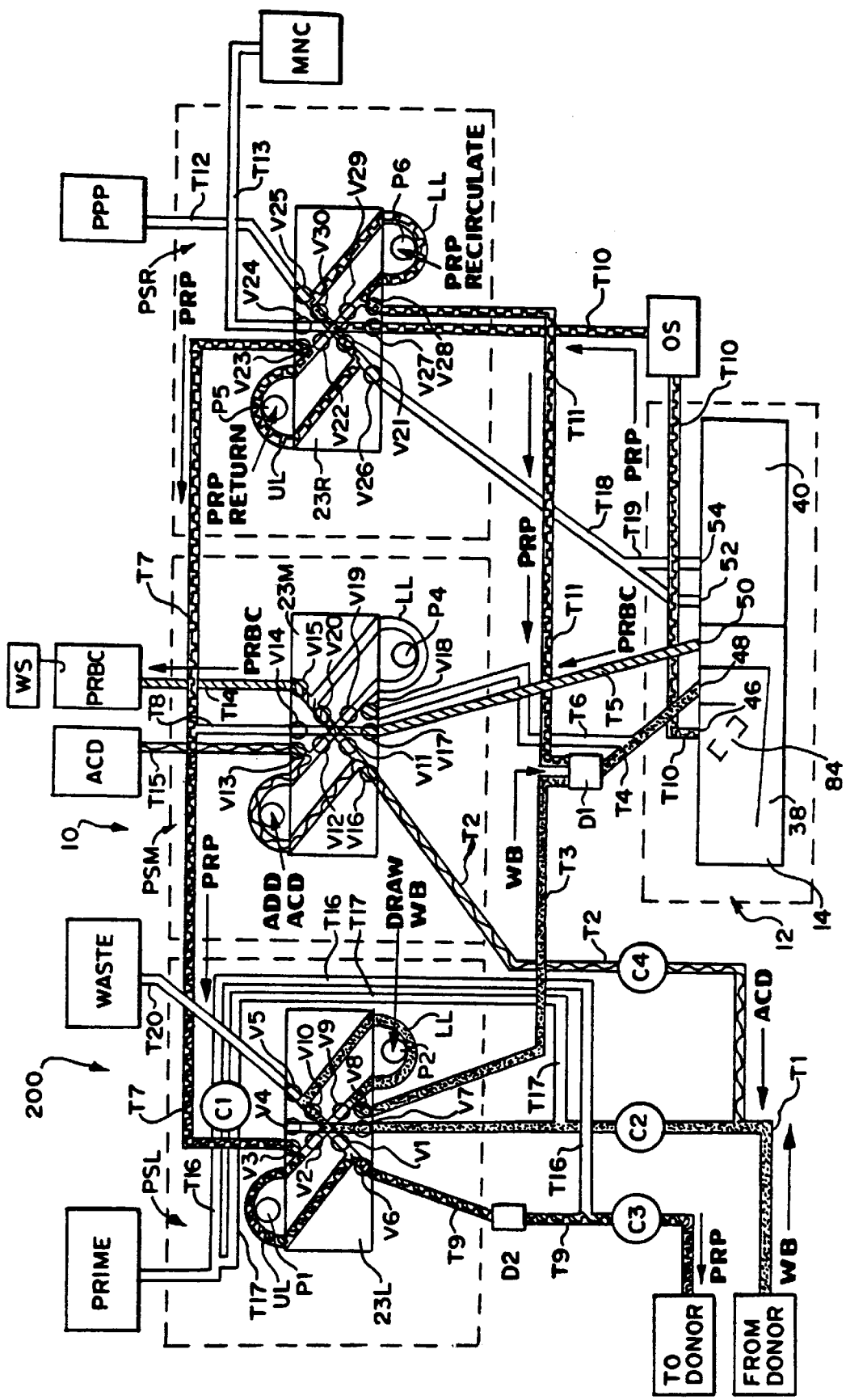
Figure 24A:
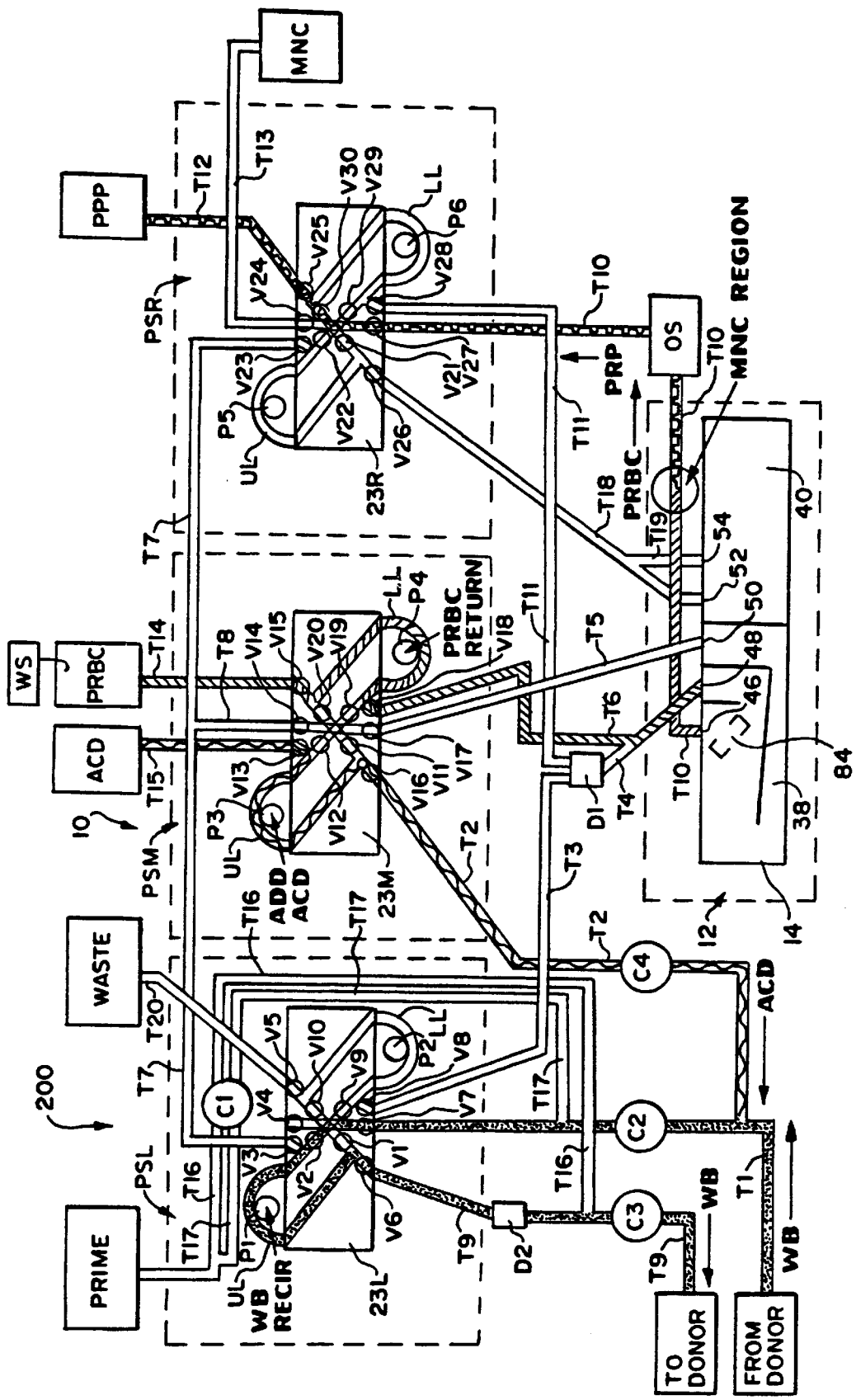
Figure 24B:
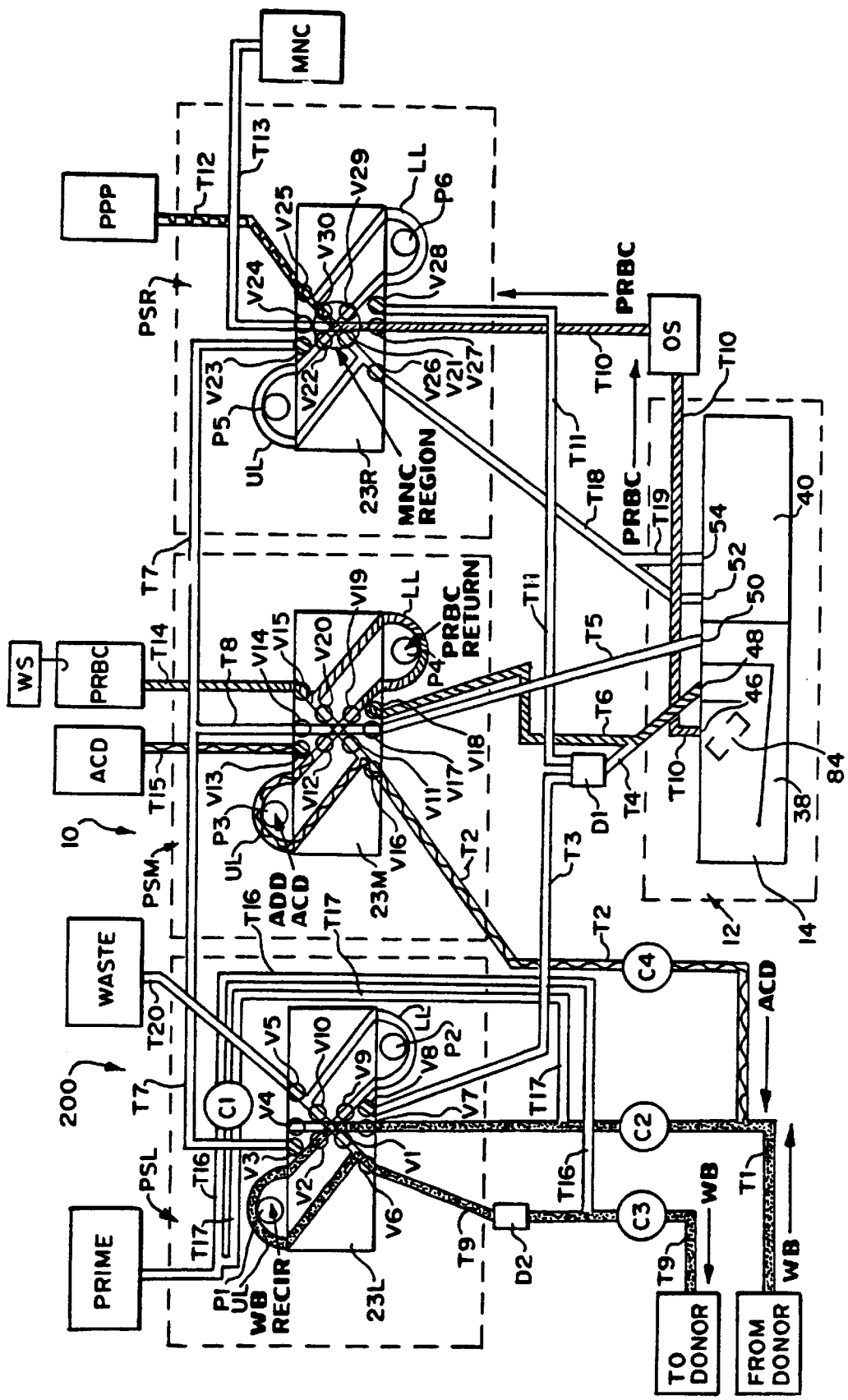
Figure 24C:
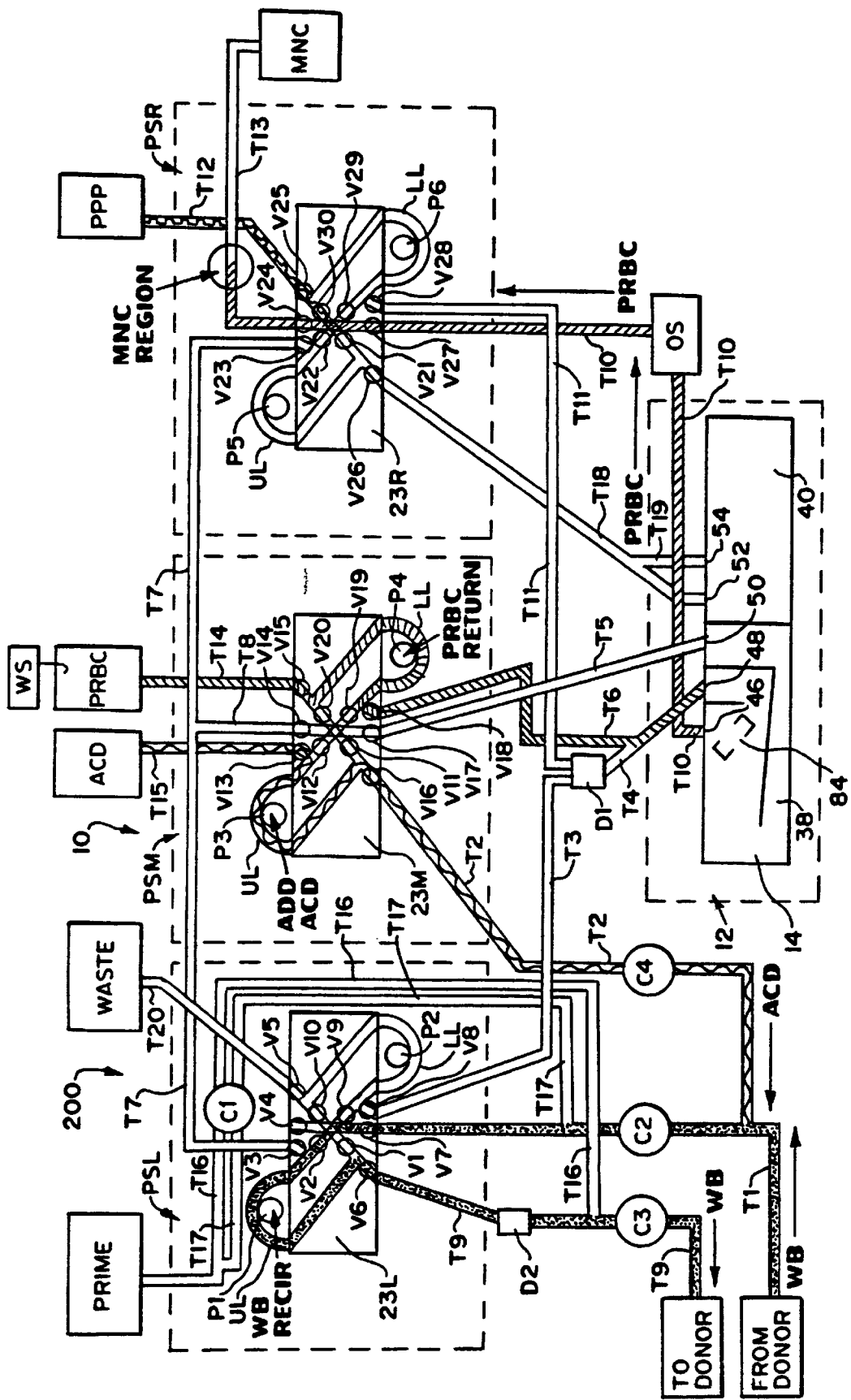
Figure 25:
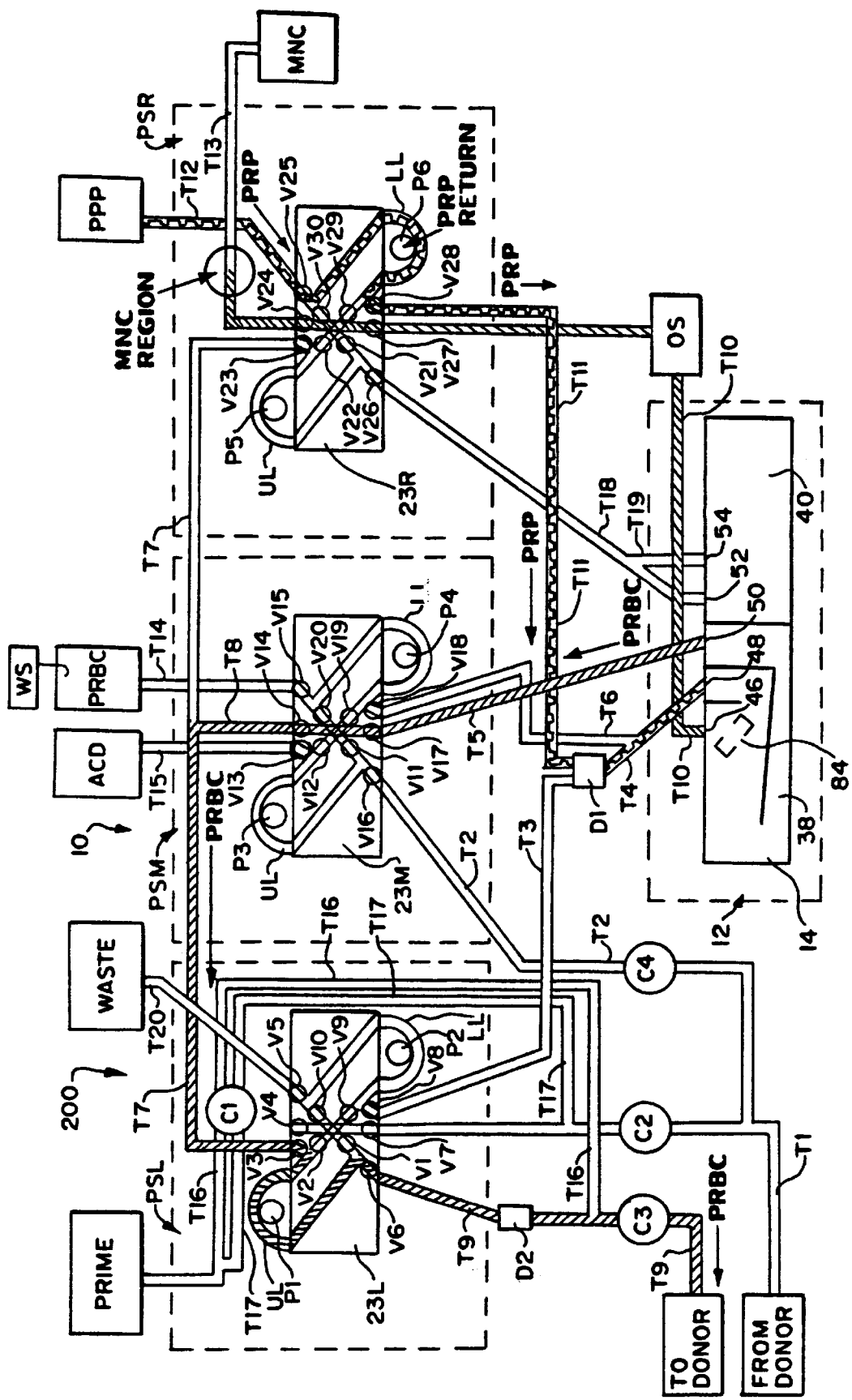
Figure 26:
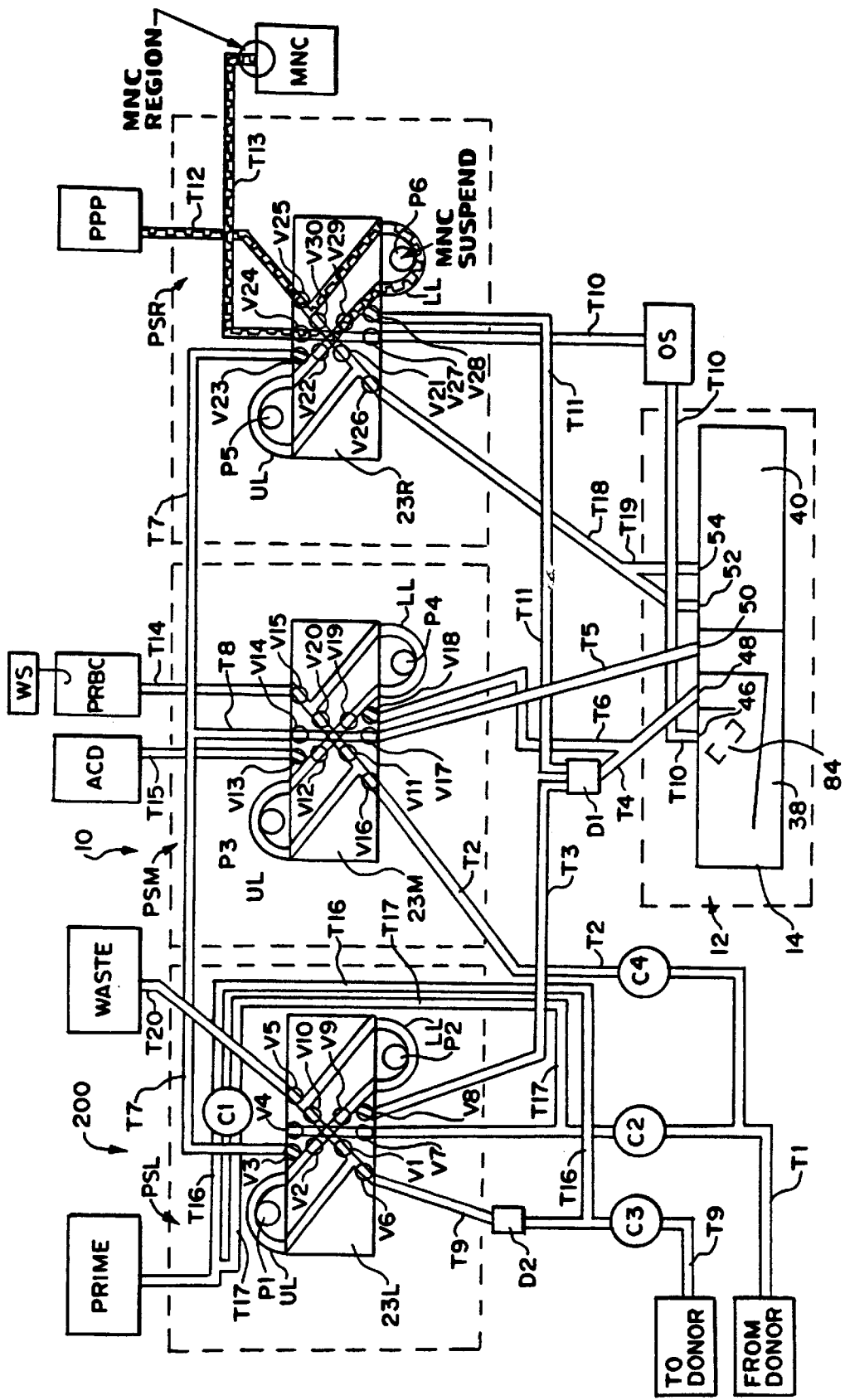
Figure 27:
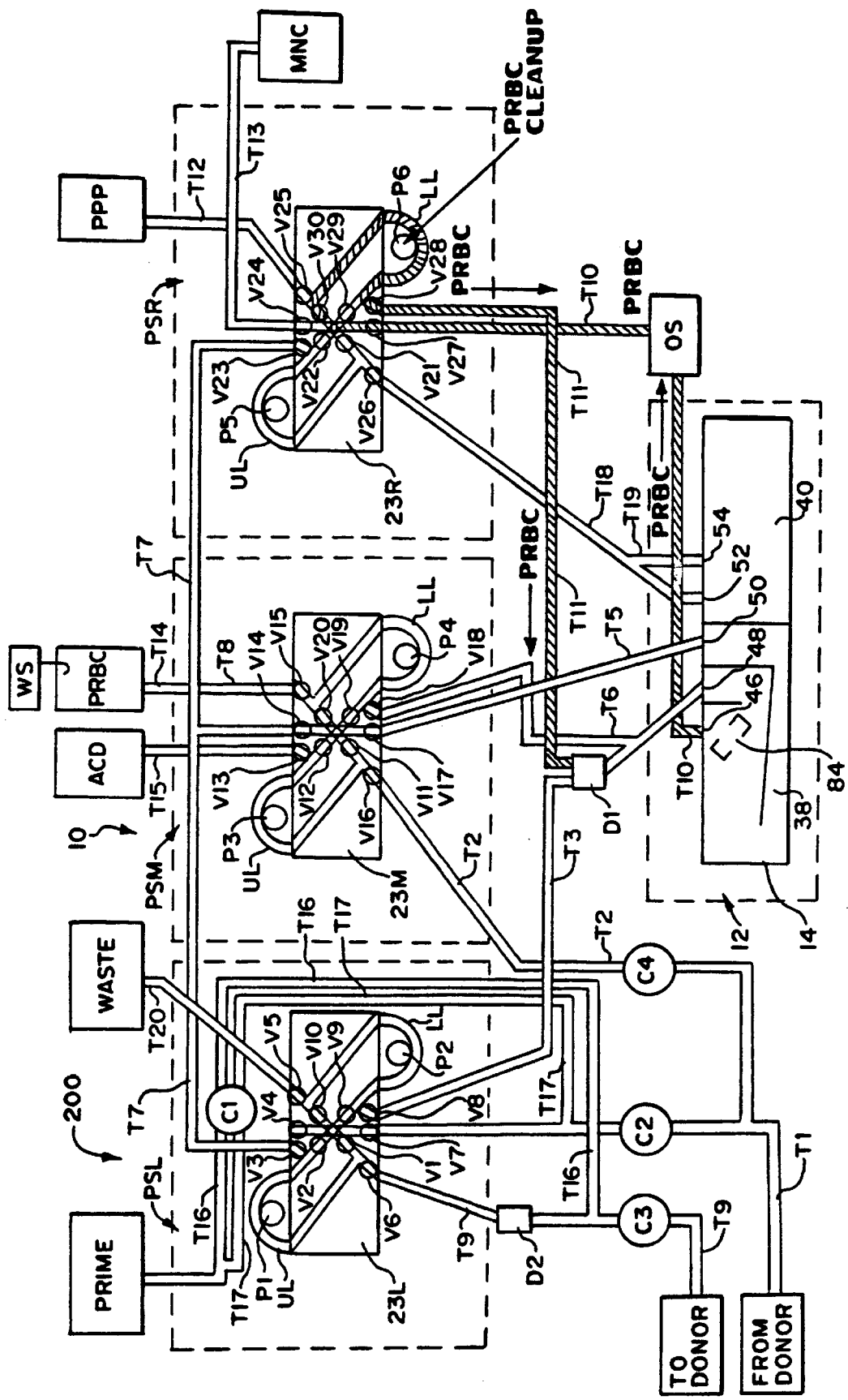
Figure 28:
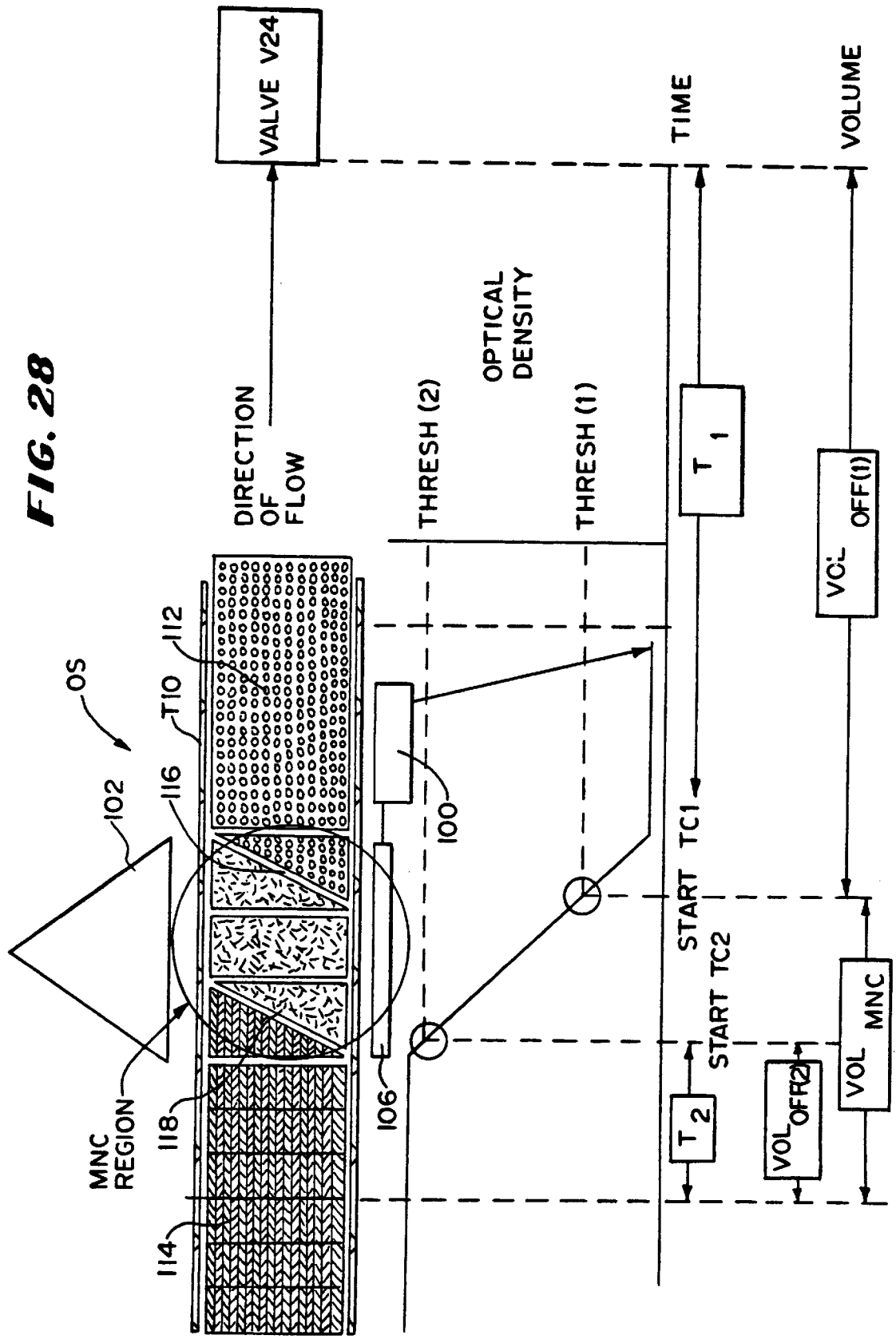
Figure 29:
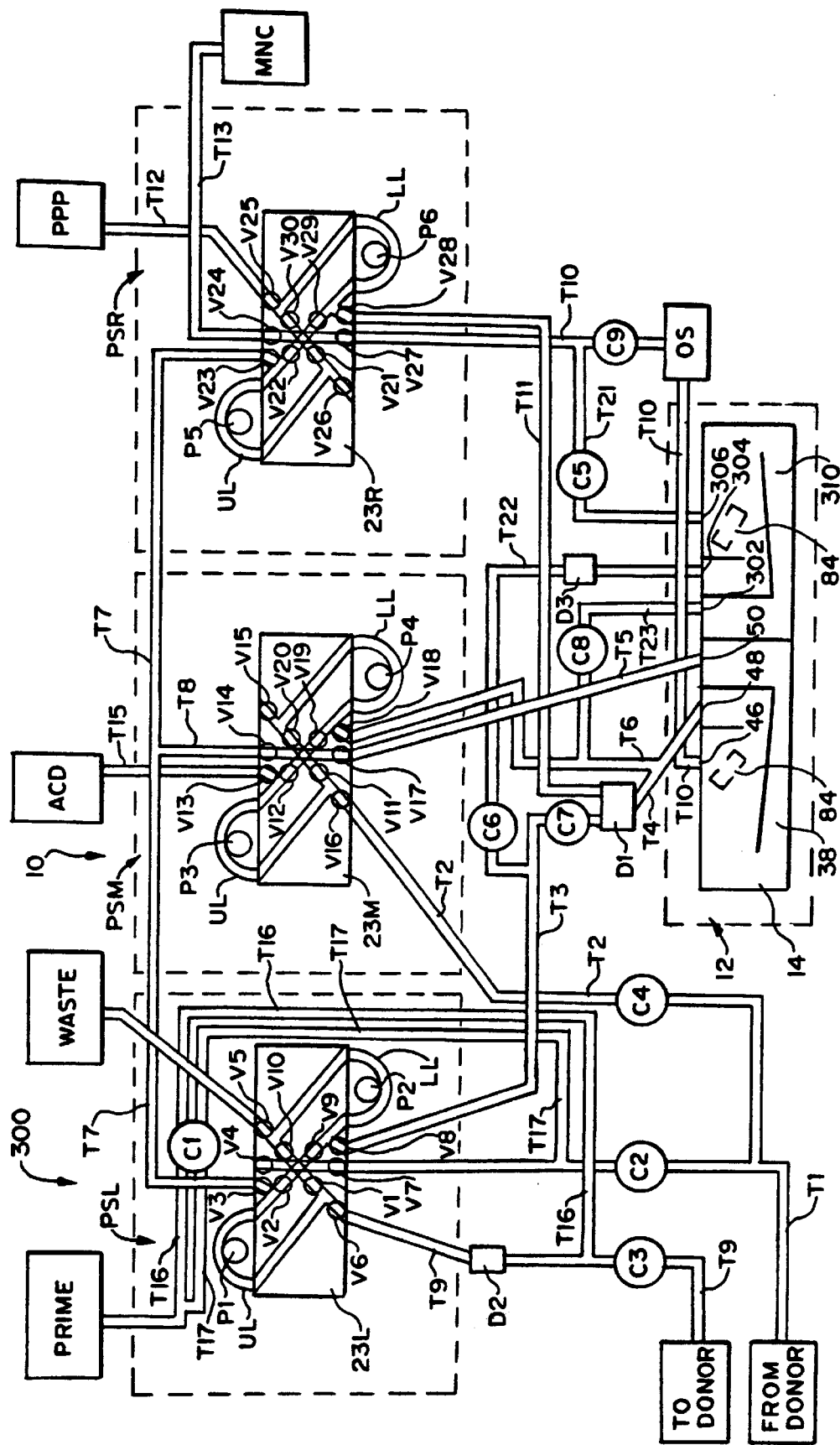
Figure 30:
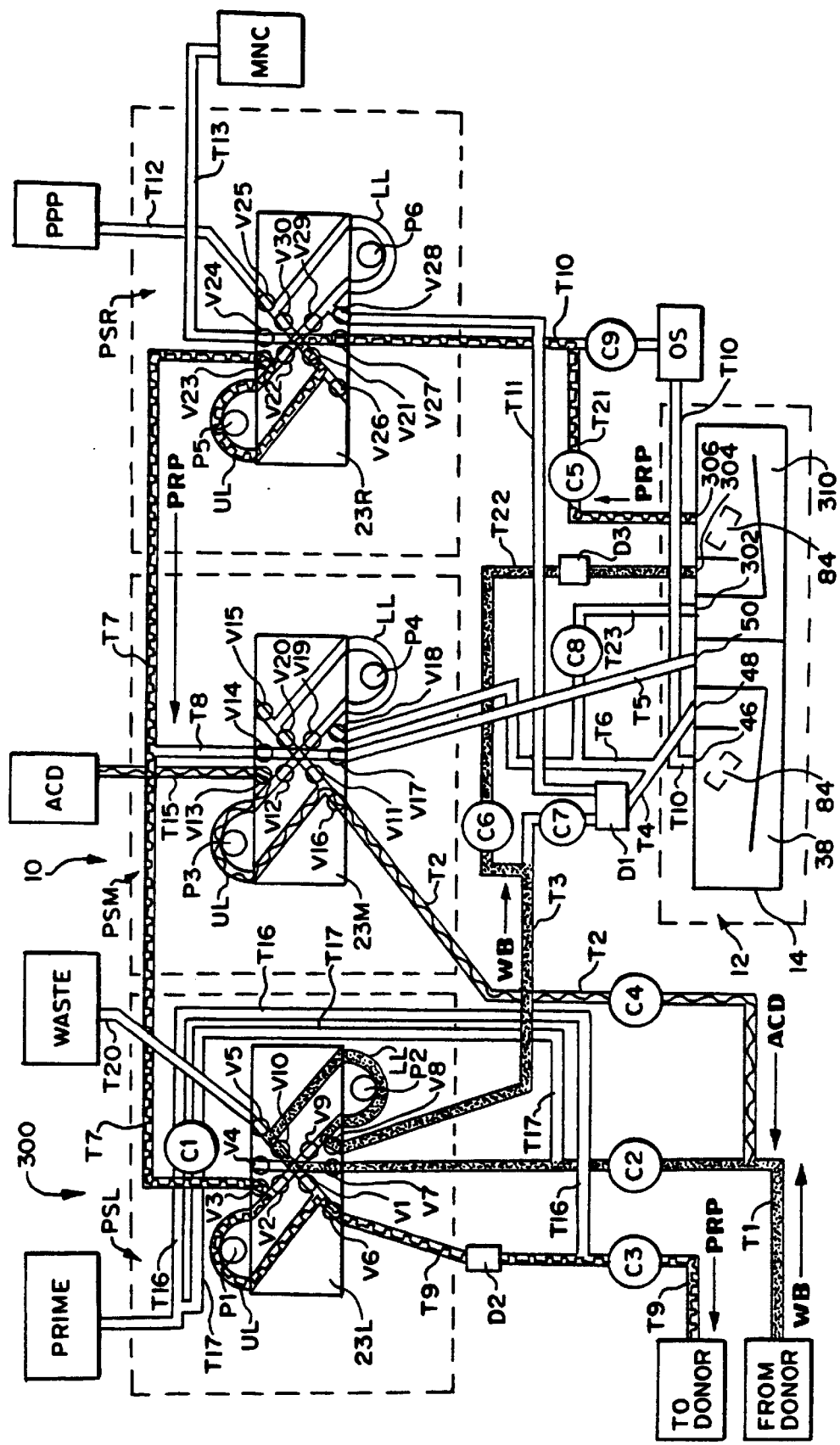
Figure 31:
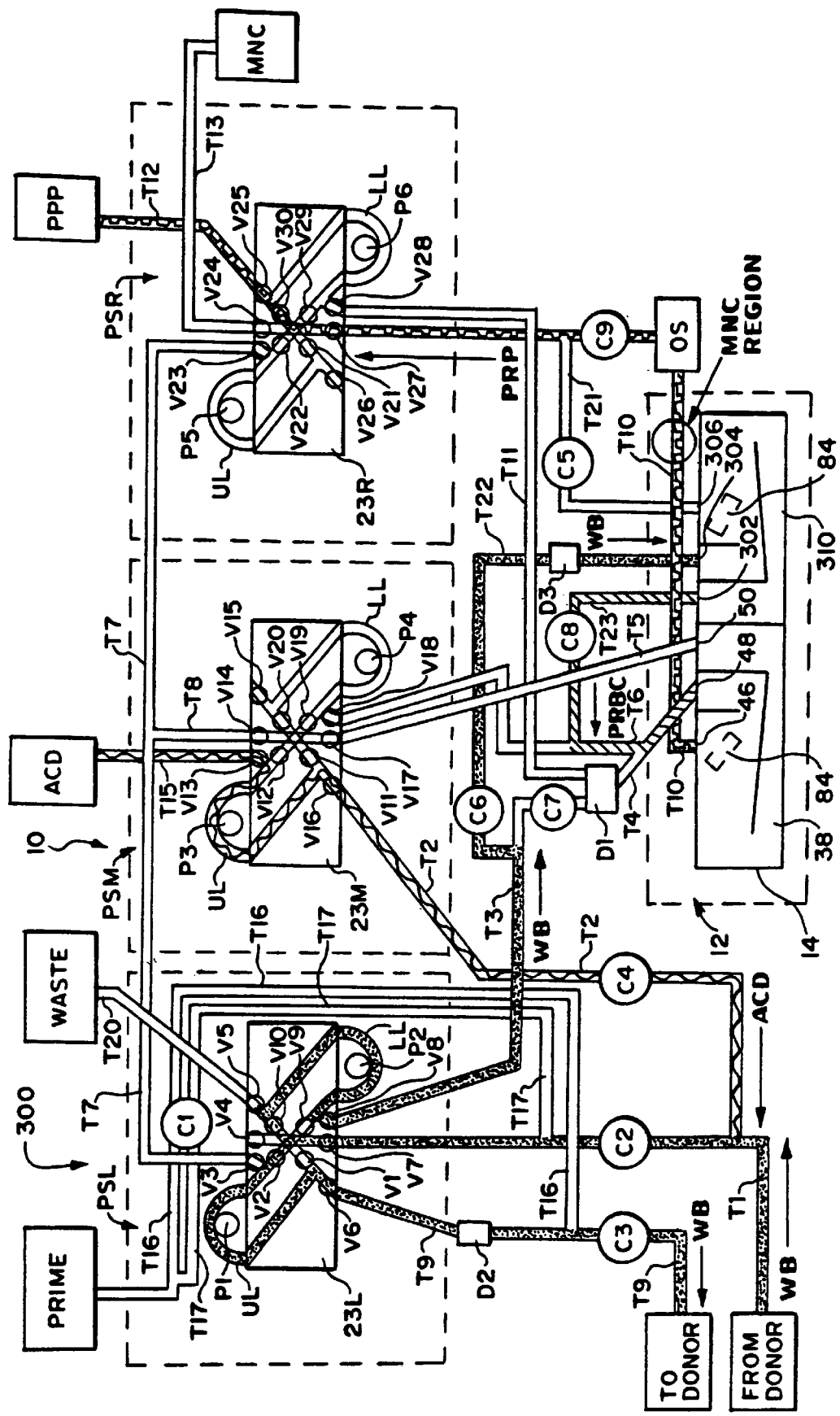

FIG. 23 is a schematic view showing the conveyance of blood components and fluids in the circuit shown in FIG. 6 during the PRBC collection phase of the procedure shown in FIG. 20;

FIG. 24A is a schematic view showing the conveyance of blood components and fluids in the circuit shown in FIG. 6 at the beginning of the MNC removal phase of the procedure shown in FIG. 20;

FIG. 24B is a schematic view showing the conveyance of blood components and fluids in the circuit shown in FIG. 6 during the MNC removal phase of the procedure shown in FIG. 20;

FIG. 24C is a schematic view showing the conveyance of blood components and fluids in the circuit shown in FIG. 6 at the end of the MNC removal phase of the procedure shown in FIG. 20;

FIG. 25 is a schematic view showing the conveyance of blood components and fluids in the circuit shown in FIG. 6 during the PRP flush phase of the procedure shown in FIG. 20;

FIG. 26 is a schematic view showing the conveyance of blood components and fluids in the circuit shown in FIG. 6 during the MNC suspension phase of the procedure shown in FIG. 20;

FIG. 27 is a schematic view showing the conveyance of blood components and fluids in the circuit shown in FIG. 6 during the clean up phase of the procedure shown in FIG. 20;

FIG. 28 is a schematic view of the optical sensor used in association with the circuit shown in FIG. 6 to sense and quantify the MNC region for harvesting;

FIG. 29 is an alternative embodiment of a fluid circuit suited for collecting and harvesting MNC;

FIG. 30 is a schematic view showing the conveyance of blood components and fluids in the circuit shown in FIG. 29 during the PRBC collection phase of the procedure shown in FIG. 20; and FIG. 31 is a schematic view showing the conveyance of blood components and fluids in the circuit shown in FIG. 29 during the MNC removal phase of the procedure shown in FIG. 20.

The invention may be embodied in several forms without departing from its spirit or essential characteristics. The scope of the invention is defined in the appended claims, rather than in the specific description preceding them. All embodiments that fall within the meaning and range of equivalency of the claims are therefore intended to be embraced by the claims.

DESCRIPTION OF THE PREFERRED EMBODIMENTS

I. The Centrifuge

Figure 1:
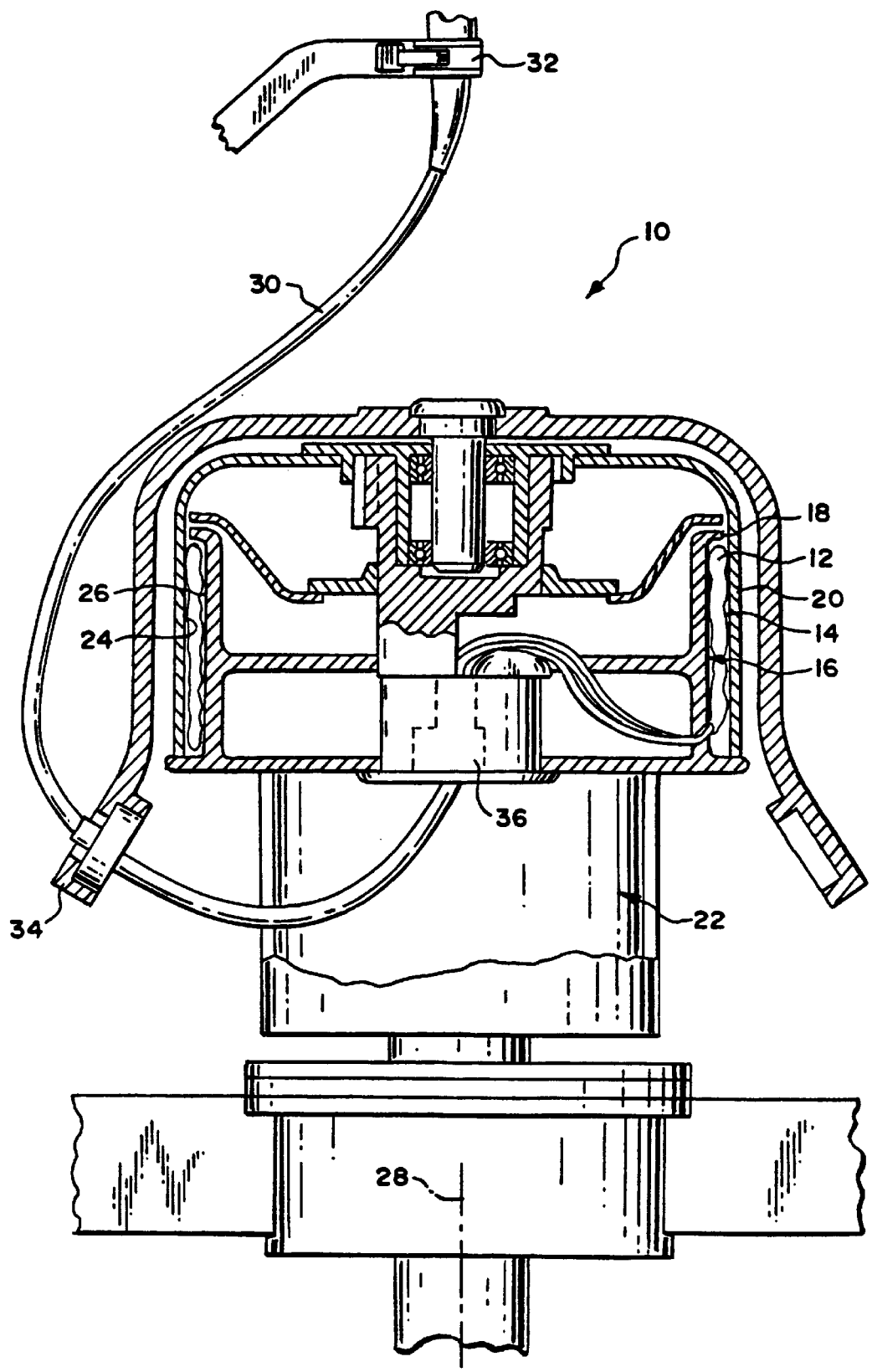
FIG. 1 is a side section view of a blood centrifuge having a separation chamber that embodies features of the invention.

FIG. 1 shows a blood centrifuge 10 having a blood processing chamber 12 suitable for harvesting mononuclear cells (MNC) from whole blood. The boundaries of the chamber 12 are formed by a flexible processing container 14 carried within an annular gap 16 between a rotating spool element 18 and bowl element 20. In the illustrated and preferred embodiment, the processing container 14 takes the form of an elongated tube (see FIG. 2), which is wrapped about the spool element 18 before use.

Further details of the centrifuge 10 are set forth in U.S. Pat. No. 5,370,802, entitled "Enhanced Yield Platelet Systems and Methods," which is incorporated herein by reference.

Figures 3A, 3B:
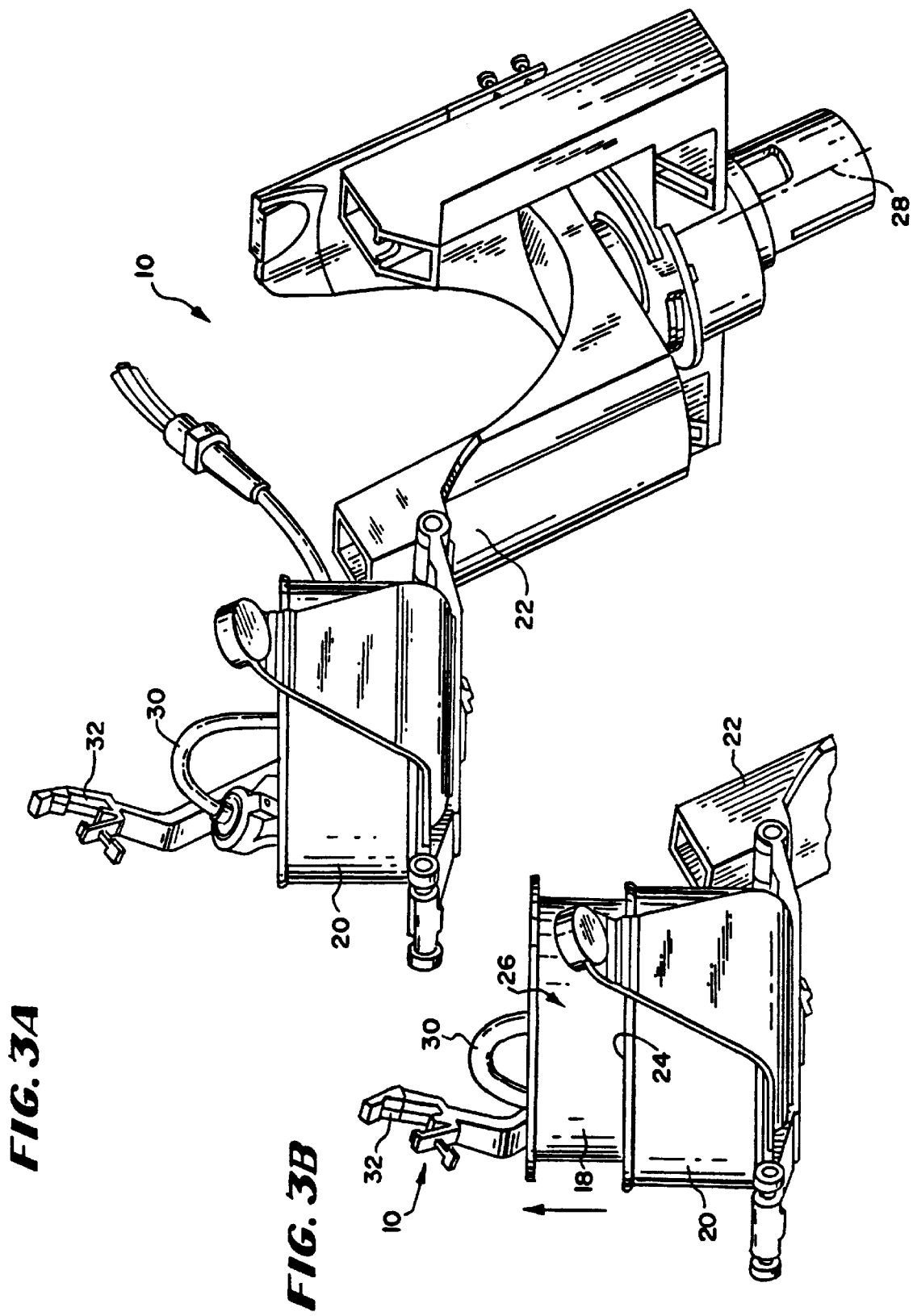
FIG. 3A is a perspective view of the centrifuge shown in FIG. 1, with the bowl and spool elements pivoted into their access position.
FIG. 3B is a perspective view of the bowl and spool elements in their mutually separation condition to allow securing the processing container shown in FIG. 2 about the spool element.

The bowl and spool elements 18 and 20 are pivoted on a yoke 22 between an upright position, as FIGS. 3A and 3B show, and a suspended position, as FIG. 1 shows.

Figure 2:
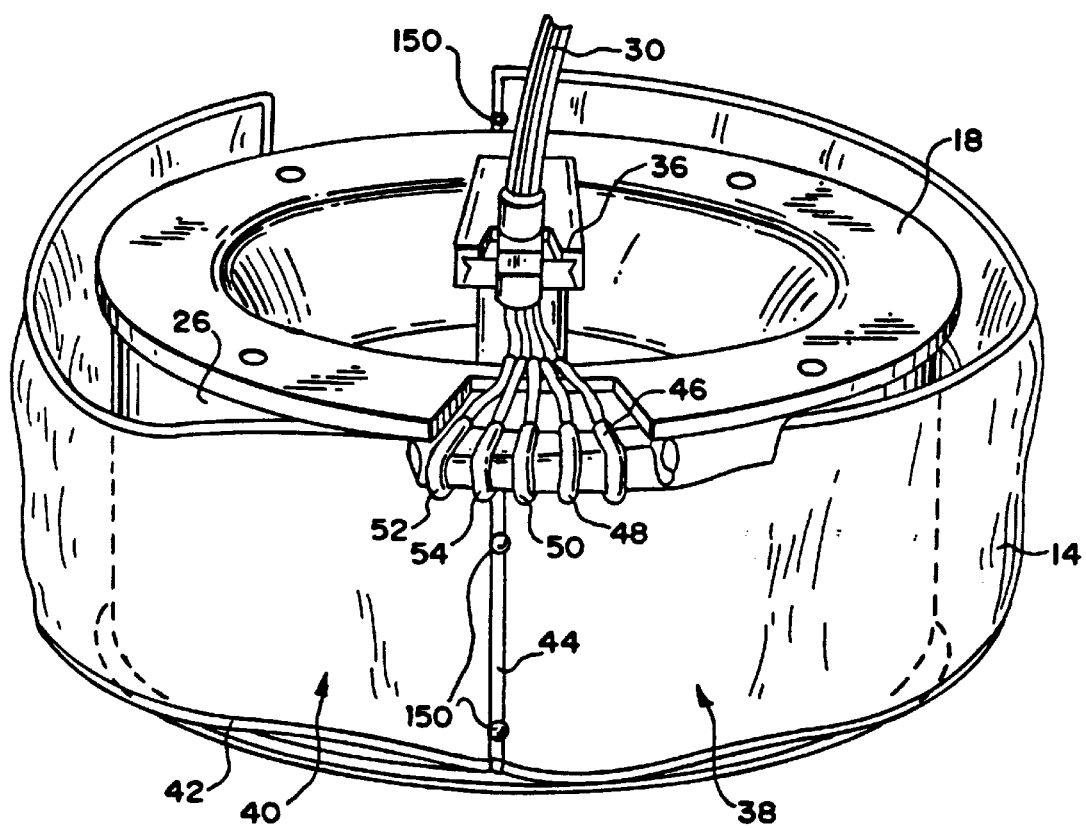
FIG. 2 shows the spool element associated with the centrifuge shown in FIG. 1, with an associated processing container wrapped about it for use.

When upright, the bowl and spool elements 18 and 20 are presented for access by the user. A mechanism permits the spool and bowl elements 18 and 20 to be opened, as FIG. 3B shows, so that the operator can wrap the container 14 about the spool element 20, as FIG. 2 shows. Pins 150 on the spool element 20 engage cutouts on the container 14 to secure the container 14 on the spool element 20.

When closed, the spool and bowl elements 18 and 20 can be pivoted into the suspended position shown in FIG. 1. In operation, the centrifuge 10 rotates the suspended bowl and spool elements 18 and 20 about an axis 28, creating a centrifugal field within the processing chamber 12.

Further details of the mechanism for causing relative movement of the spool and bowl elements 18 and 20 as just described are disclosed in U.S. Pat. No. 5,360,542 entitled "Centrifuge With Separable Bowl and Spool Elements Providing Access to the Separation Chamber," which is incorporated herein by reference.

The radial boundaries of the centrifugal field (see FIG. 1) are formed by the interior wall 24 of the bowl element 18 and the exterior wall 26 of the spool element 20. The interior bowl wall 24 defines the high-G wall. The exterior spool wall 26 defines the low-G wall.

II. The Processing Container

In the illustrated embodiment (see FIG. 4), a first peripheral seal 42 forms the outer edge of the container 14. A second interior seal 44 extends generally parallel to the rotational axis 28, dividing the container 14 into two compartments 38 and 40.

In use, whole blood is centrifugally separated in the compartment 38. In use, the compartment 40 carries a liquid, such as saline, to counter-balance the compartment 38. In the embodiment shown in FIG. 4, the compartment 38 is larger than the compartment 40 by a volumetric ratio of about 1 to 1.2.

Three ports 46, 48, and 50 communicate with the processing compartment 38, to convey whole blood and its components. Two additional ports 52 and 54 communicate with the ballast compartment 40 to convey the counter-balancing fluid.

III. The Fluid Processing Circuit

A fluid circuit 200 (see FIG. 4) is coupled to the container 14. FIG. 5 shows the general layout of the fluid circuit 200, in terms of an array of flexible tubing, liquid source and collection containers, in-line pumps, and clamps, all of which will be described in greater detail later. FIG. 6 shows the details of the fluid circuit 200 in schematic form.

In the illustrated embodiment, left, middle, and right cassettes, respectively 23L, 23M, and 23R, centralize many of the valving and pumping functions of the fluid circuit 200. The left, middle, and right cassettes 23L, 23M, and 23R mate with left, middle, and right pump stations on the centrifuge 10, which are designated, respectively, PSL, PSM, and PSR.

A. The Cassettes

Each cassette 23L, 23M, and 23R is constructed the same, so a description of one cassette 23L is applicable to all cassettes. FIGS. 7 and 8 show the structural details of the cassette 23L.

The cassette 23L comprises a molded plastic body 202. Liquid flow channels 208 are integrally molded into on the front side 204 of the body 202. A rigid panel 214 covers and seals the front body side 204.

Valve stations 210 are molded into the back side 206 of the cassette body 202. A flexible diaphragm 212 covers and seals the back side 206 of the body 202.

Figure 9:
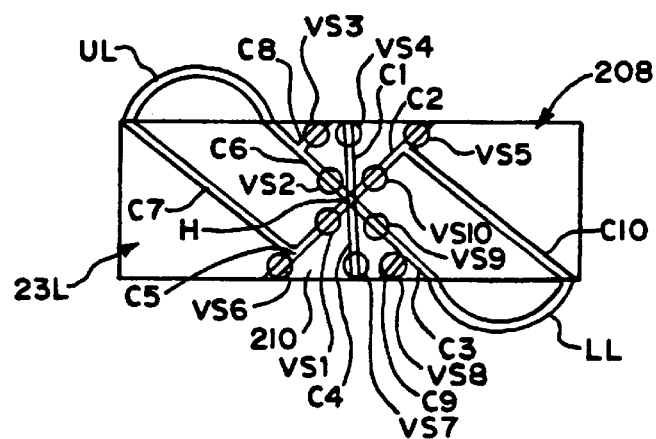
FIG. 9 is a schematic view of the flow channels and valve stations formed within the cassette shown in FIG. 7.

FIG. 9 schematically shows a representative array of flow channels 208 and valve stations 210 for each cassette. As shown, channels C1 to C6 intersect to form a star array, radiating from a central hub H. Channel C7 intersects channel C5; channel C8 intersects channel C6; channel C9 intersects channel C3; and channel C10 intersects channel C2. Of course, other channel patterns can be used.

In this arrangement, valve stations VS1, VS2, VS9, and VS10 are located in, respectively, channels C2, C3, C5, and C6 immediately next to their common intersection at the hub H. Valve stations VS3, VS4, VS5, VS6, VS7, and VS8 are located at the outer extremities of channels C8, C1, C2, C5, C4, and C3, respectively.

Each cassette 23L carries an upper flexible tubing loop UL, which extends outside the cassette 23L between channels C7 and C6, and a lower tubing loop LL, which extends outside the cassette between channels C3 and C10. In use, the tube loops UL and LL engage the peristaltic pump rotors of the pumps on the associated pump station.

B. The Pumping Stations

Figure 10:
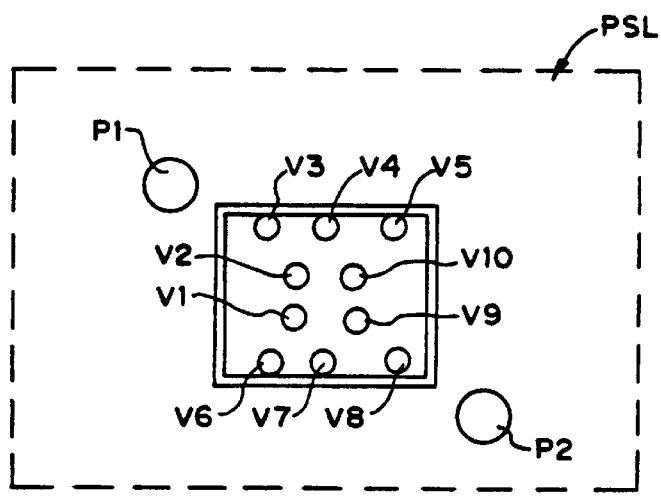
FIG. 10 is a schematic view of a pump station intended to receive a cassette of the type shown in FIG. 7.
Figure 12:
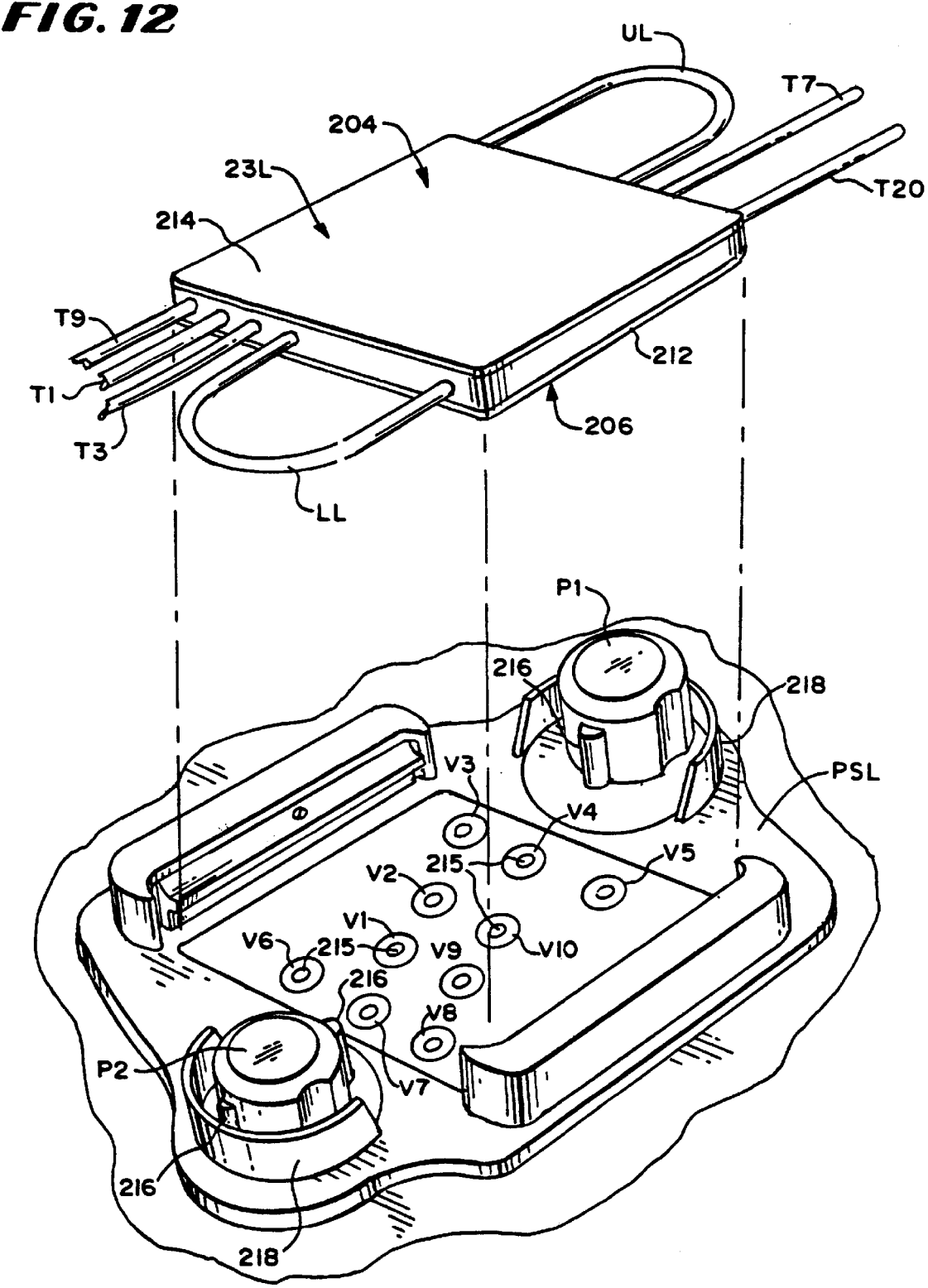
FIG. 12 is a perspective view of a cassette and a pump station which form a part of the fluid circuit shown in FIG. 6.

The pump stations PSL, PSM, and PSR are, like the cassettes 23L, 23M, and 23R, identically constructed, so a description of one station PSL is applicable to all. FIG. 12 shows the structural details of the left pump station PSL. FIG. 10 shows the left pump station PSL in a more schematic form.

The station PSL includes two peristaltic pumps, for a total of six pumps in the circuit 200, which are designated P1 to P6 (see FIG. 6). The station PSL also includes an array of ten valve actuators (which FIG. 10 shows), for a total of thirty valve actuators in the circuit 200, which designated VA1 to VA30 (see FIG. 6).

In use (see FIG. 11), the tube loops UL and LL of cassette 23L engage pumps P1 and P2 of the left pump station PSL. In like fashion (as FIG. 6 shows), the tube loops UL and LL of the middle cassette 23M engage pumps P3 and P4. The tube loops UL and LL of the right cassette 23L engage pumps P5 and P6.

Figure 11:
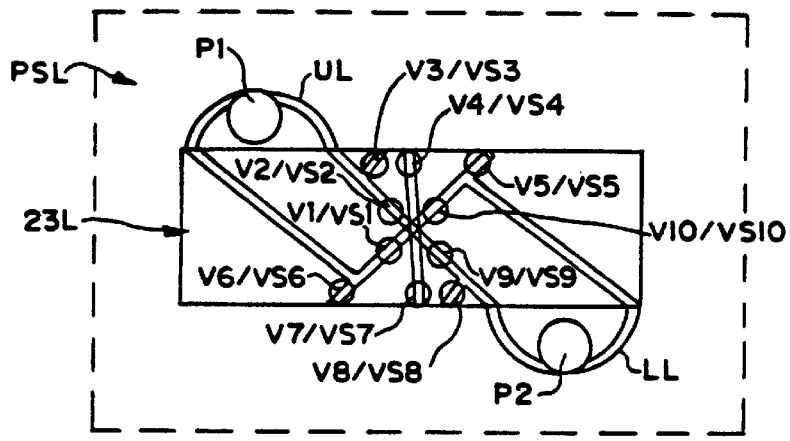
FIG. 11 is a schematic view of the cassette shown in FIG. 9 mounted on the pump station shown in FIG. 10.

As FIG. 11 shows, the valve stations VS1 to VS10 of the cassette 23L align with the valve actuators V1 to V10 of the left pump station PSL. As FIG. 6 shows, the valve stations of the middle and right cassettes 23M and 23R likewise align with the valve actuators of the respective middle and right pump stations PSM and PSR.

The following Table 1 summarizes the operative association of the pump station valve actuators V1 to V30 to the cassette valve stations S1 to VS10 shown in FIG. 6.

TABLE 1

Alignment of Cassette Valve Stations to Valve Actuators

| Valve Chambers | Left Cassette 23L | Middle Cassette 23M | Right Cassette 23R |
|---|---|---|---|
| VS1 | Valve Actuator V1 | Valve Actuator V11 | Valve Actuator V21 |
| VS2 | Valve Actuator V2 | Valve Actuator V12 | Valve Actuator V22 |
| V53 | Valve Actuator V3 | Valve Actuator V13 | Valve Actuator V23 |
| VS4 | Valve Actuator V4 | Valve Actuator V14 | Valve Actuator V24 |

TABLE 1-continued

Alignment of Cassette Valve Stations to Valve Actuators

| Valve Chambers | Left Cassette 23L | Middle Cassette 23M | Right Cassette 23R |
|---|---|---|---|
| VS5 | Valve Actuator V5 | Valve Actuator V15 | Valve Actuator V25 |
| VS6 | Valve Actuator V6 | Valve Actuator V16 | Valve Actuator V26 |
| VS7 | Valve Actuator V7 | Valve Actuator V17 | Valve Actuator V27 |
| VS8 | Valve Actuator V8 | Valve Actuator V18 | Valve Actuator V28 |
| VS9 | Valve Actuator V9 | Valve Actuator V19 | Valve Actuator V29 |
| VS10 | Valve Actuator V10 | Valve Actuator V20 | Valve Actuator V30 |

The cassettes 23L, 23M, and 23R are mounted on their respective pump stations PSL, PSM, PSR with their back sides 206 down, so that 20 the diaphragms 212 face and engage the valve actuators. The valve actuators Vn are solenoid-actuated rams 215 (see FIG. 12), which are biased toward a valve closing position. The valve actuators Vn are patterned to align with the cassette valve stations VSn in the manner set forth in Table 1. When a given ram 215 is energized, the associated cassette valve station is opened, allowing through-passage of liquid. When the ram 215 is not energized, it displaces the diaphragm 212 into the associated valve station, blocking passage of liquid through the associated valve station.

In the illustrated embodiment, as FIG. 12 shows, the pumps P1 to P6 on each pump station PSL, PSM, and PSR include rotating peristaltic pump rotors 216. The rotors 216 can be moved between a retracted condition (shown in FIG. 13), out of engagement with the respective tube loop, and an operating condition (shown in FIG. 14), in which the rotors 216 engage the respective tube loop against a pump race 218.

Figure 14:
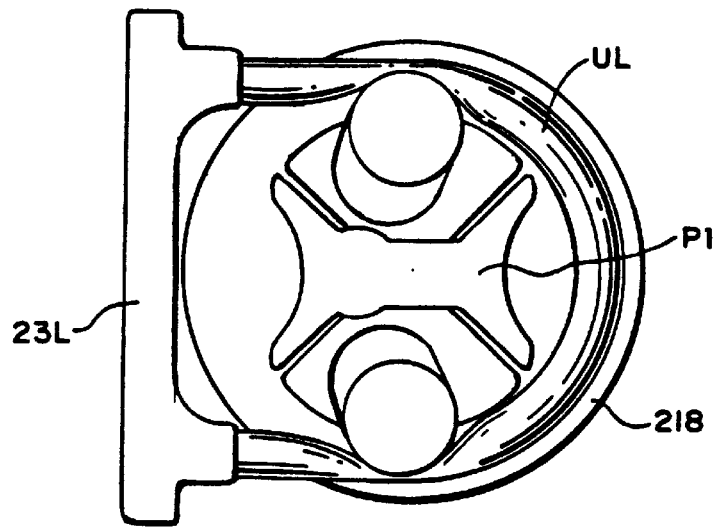
FIG. 14 is a top view of a peristaltic pump that forms a part of the fluid circuit shown in FIG. 6, with the pump rotor in an extended position engaging pump tubing.

The pumps P1 and P6 can thereby be operated in three conditions:

(i) in a pump on condition, during which the pump rotors 216 rotate and are in their operating position to engage the pump tubing against the pump race 218 (as FIG. 14 shows). The rotating pump rotors 216 therefore convey fluid in a peristaltic fashion through the tubing loop.

Figure 13:
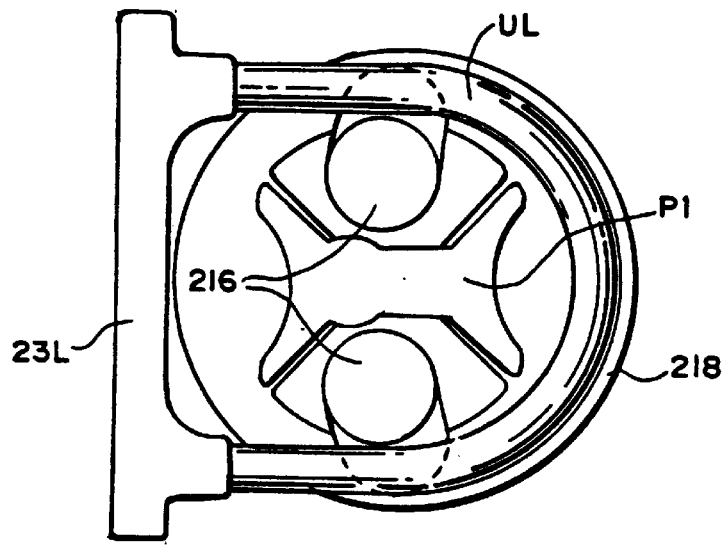
FIG. 13 is a top view of a peristaltic pump that forms a part of the fluid circuit shown in FIG. 6, with the pump rotor in a retracted position.

(ii) in an opened, pump off condition, during which the pump rotors 216 are not rotated and are in their retracted position, so as not to engage the pump tubing loop (as FIG. 13 shows). The opened, pump off condition therefore permits fluid flow through the pump tube loop in the absence of pump rotor rotation.

(iii) in a closed, pump off condition, during which the pump rotors 216 are not rotated, and the pump rotors are in the operating condition. The stationary pump rotors 216 thereby engage the pump tubing loop, and serve as a clamp to block fluid flow through the pump tubing loop.

Of course, equivalent combinations of pump conditions can be achieved using peristaltic pump rotors that do not retract, by suitable placement of clamps and tubing paths upstream and downstream of the pump rotors.

Further structural details of the cassettes 23L, 23M, 23R, the peristaltic pumps P1 to P6, and the valve actuators V1 to V30 are not essential to the invention. These details are described in U. S. Pat. No. 5,427,509, entitled "Peristaltic Pump Tube Cassette with Angle Port Tube Connectors," which is incorporated herein by reference.

C. The Fluid Flow Tubing

The fluid circuit 200 further includes lengths of flexible plastic tubing, designated T1 to T20 in FIG. 6. The flexible tubing T1 to T20 couple the cassettes 23L, 23M, and 23R to the processing container 14, to external source and collection bags or containers, and to the blood donor/patient.

The fluid flow function of the tubing T1 to T20 in connection with collecting and harvesting MNC will be described later. The following summarizes, from a structural standpoint, the attachment of the tubing T1 to T20, as shown in FIG. 6:

Tubing T1 extends from the donor/patient (via a conventional phlebotomy needle, not shown) through an external clamp C2 to channel C4 of the left cassette 23L.

Tubing T2 extends from tube T1 through an external clamp C4 to channel C5 of the middle cassette 23M.

Tubing T3 extends from an air detection chamber D1 to channel C9 of the left cassette 23L.

Tubing T4 extends from the drip chamber D1 to port 48 of the processing container 14.

Tubing T5 extends from port 50 of the processing container 14 to channel C4 of the middle cassette 23M.

Tubing T6 extends from channel C9 of the middle cassette 23M to join tubing T4 downstream of the chamber D1.

Tubing T7 extends from channel C8 of the right cassette 23R to channel C8 of the left cassette 23L.

Tubing T8 extends from channel C1 of the middle cassette 23M to join tubing T7.

Tubing T9 extends from channel C5 of the left cassette 23L through an air detection chamber D2 and an external clamp C3 to the donor/patient (via a conventional phlebotomy needle, not shown).

Tubing T10 extends from port 46 of the processing container 14, through an in line optical sensor OS to channel C4 of the right cassette 23R.

Tubing T11 extends from channel C9 of the right cassette 23R to the chamber D1.

Tubing T12 extends from channel C2 of the right cassette 23R to a container intended to receive platelet-poor plasma, designated PPP. A weight scale (not shown) senses weight of the container PPP for the purpose of deriving fluid volume changes.

Tubing T13 extends from channel C1 of the right cassette 23R to a container intended to receive mono-nuclear cells, designated MNC.

Tubing T14 extends from channel C2 of the middle cassette 23M to a container intended to receive packed red blood cells, designated PRBC. A weight scale WS senses weight of the container PRBC for the purpose of deriving fluid volume changes.

Tubing T15 extends from a container of anticoagulant, designated ACD, to channel C8 of the middle cassette 23M. A weight scale (not shown) senses weight of the container ACD for the purpose of deriving fluid volume changes.

Tubing T16 and T17 extend from a container of priming liquid, such as saline, designated PRIME, bypassing all cassettes 23L, 23M, and 23R, through an external clamp C1, and intersecting, respectively, tubing T9 (between the air detection chamber D2 and the clamp C3) and tubing T1 (upstream of clamp C3). A weight scale (not shown) senses weight of the container PRIME for the purpose of deriving fluid volume changes.

Tubing T18 extends from the port 52 of the processing container 14 to channel C5 of the right cassette 23R.

Tubing T19 extends from the port 54 of the processing container 14 to intersect tubing T18.

Tubing T20 extends from channel C2 of the left cassette 23L to a container intended to receive waste priming fluid, designated WASTE. A weight scale (not shown) senses weight of the container WASTE for the purpose of deriving fluid volume changes.

Portions of the tubing are joined in umbilicus 30 (see FIG. 1). The umbilicus 30 provides fluid flow communication between the interior of the processing container 14 within the centrifugal field and other stationary components of the circuit 200 located outside the centrifugal field. A non-rotating (zero omega) holder 32 holds the upper portion of the umbilicus 30 in a non-rotating position above the suspended spool and bowl elements 18 and 20. A holder 34 on the yoke 22 rotates the mid-portion of the umbilicus 30 at a first (one omega) speed about the suspended spool and bowl elements 18 and 20. Another holder 36 rotates the lower end of the umbilicus 30 at a second speed twice the one omega speed (the two omega speed), at which the suspended spool and bowl elements 18 and 20 also rotate. This known relative rotation of the umbilicus 30 keeps it untwisted, in this way avoiding the need for rotating seals.

IV. Separation in the Blood Processing Chamber
(An Overview)

Before explaining the details of the procedure by which MNC are collected using the container 14 and the fluid circuit 200, the fluid dynamics of whole blood separation in the processing compartment 38 will first be generally described, with reference principally to FIGS. 4 and 15 to 17.

Figure 4:
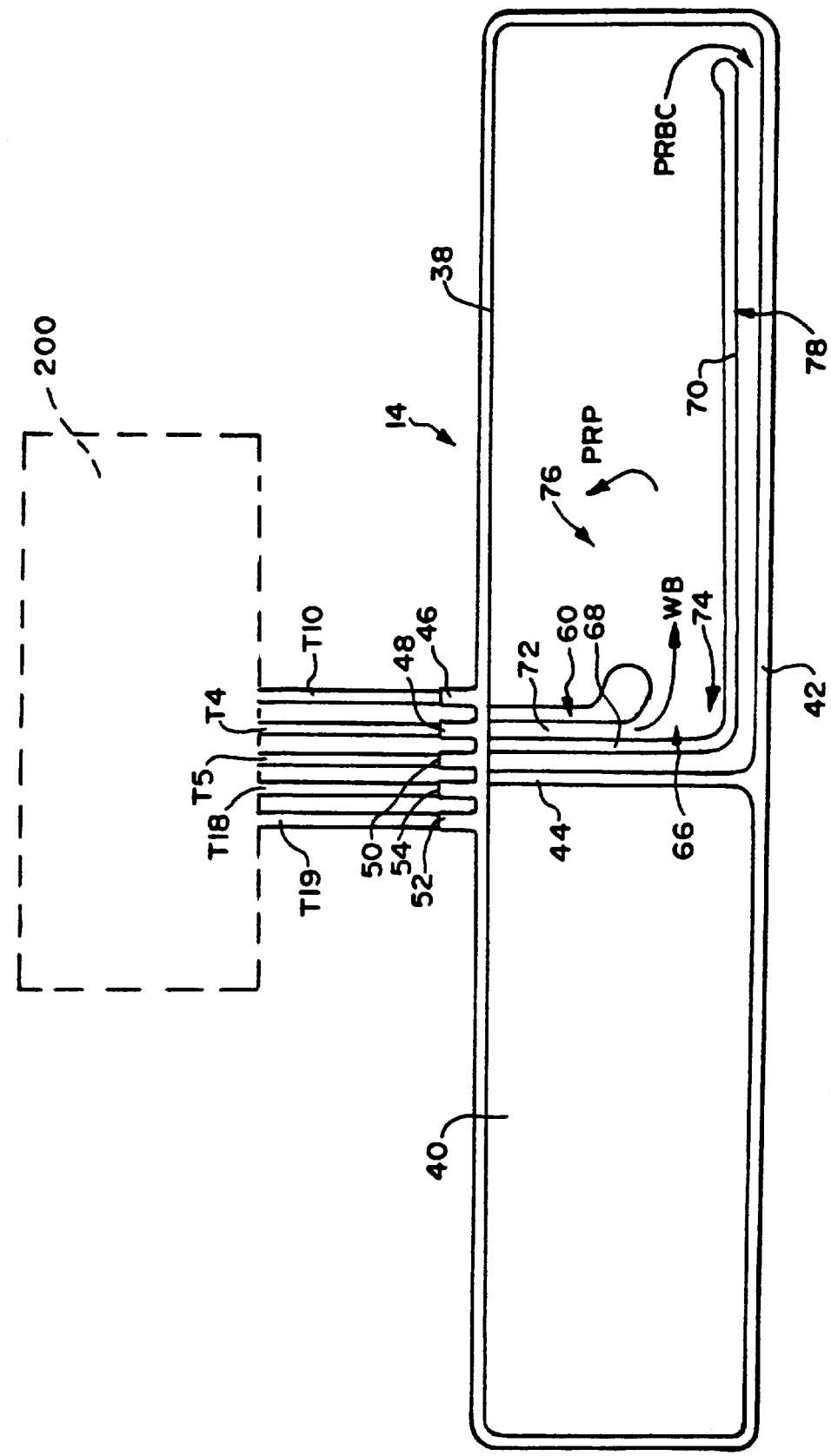
FIG. 4 is a plan view of the processing container shown in FIG. 2.
Figure 5:
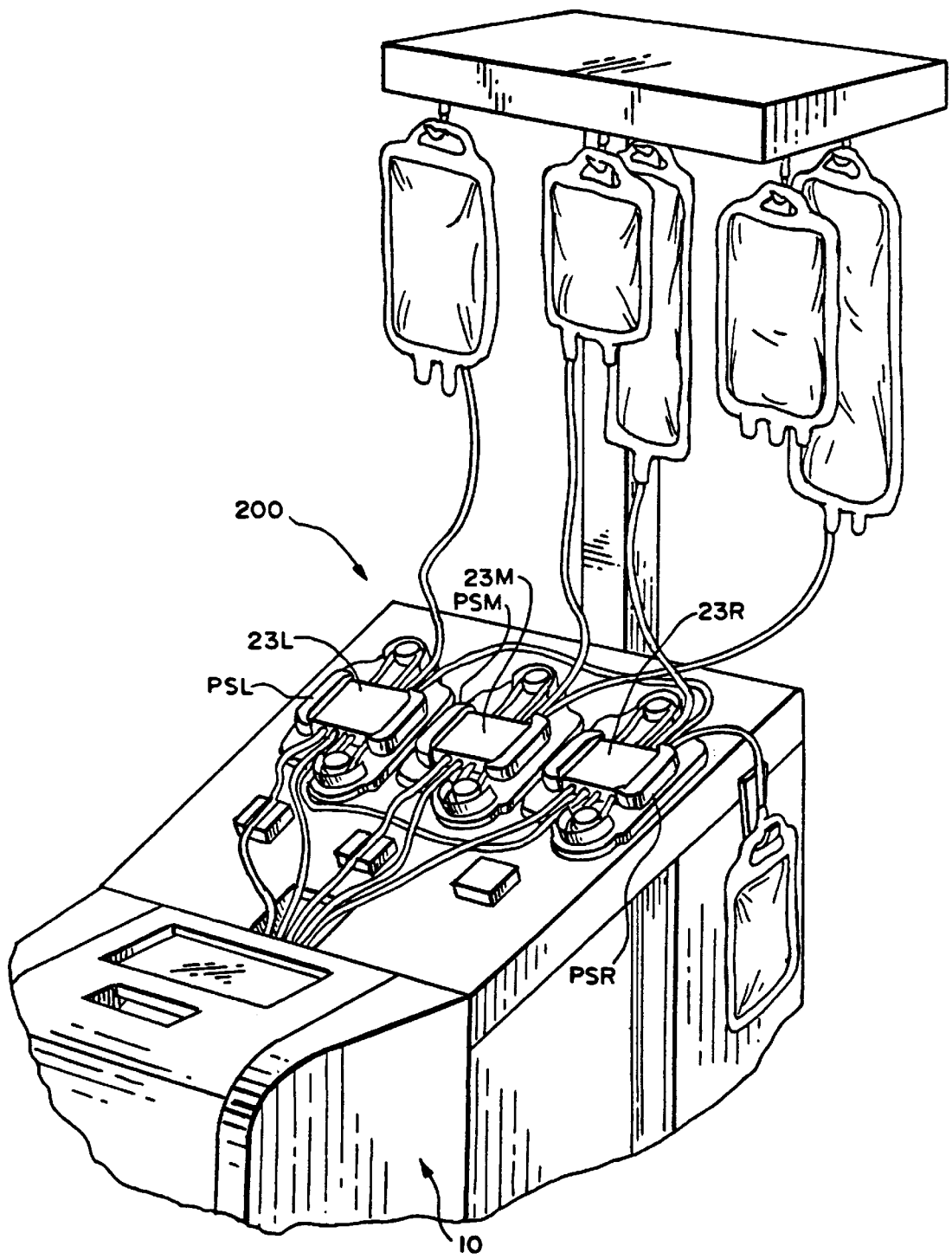
FIG. 5 is a perspective view of a fluid circuit associated with the processing container, which comprises cassettes mounted in association with pump stations on the centrifuge.

Referring first to FIG. 4, anticoagulated whole blood (WB) is drawn from the donor/patient and conveyed into the processing compartment through the port 48. The blood processing compartment 38 includes a interior seals 60 and 66, which form a WB inlet passage 72 that leads into a WB entry region 74.

As WB follows a circumferential flow path in the compartment 38 about the rotational axis 28. The sidewalls of the container 14 expand to conform to the profiles of the exterior (low-G) wall 26 of the spool element 18 and the interior (high-G) wall 24 of the bowl element 20.

Figure 17:
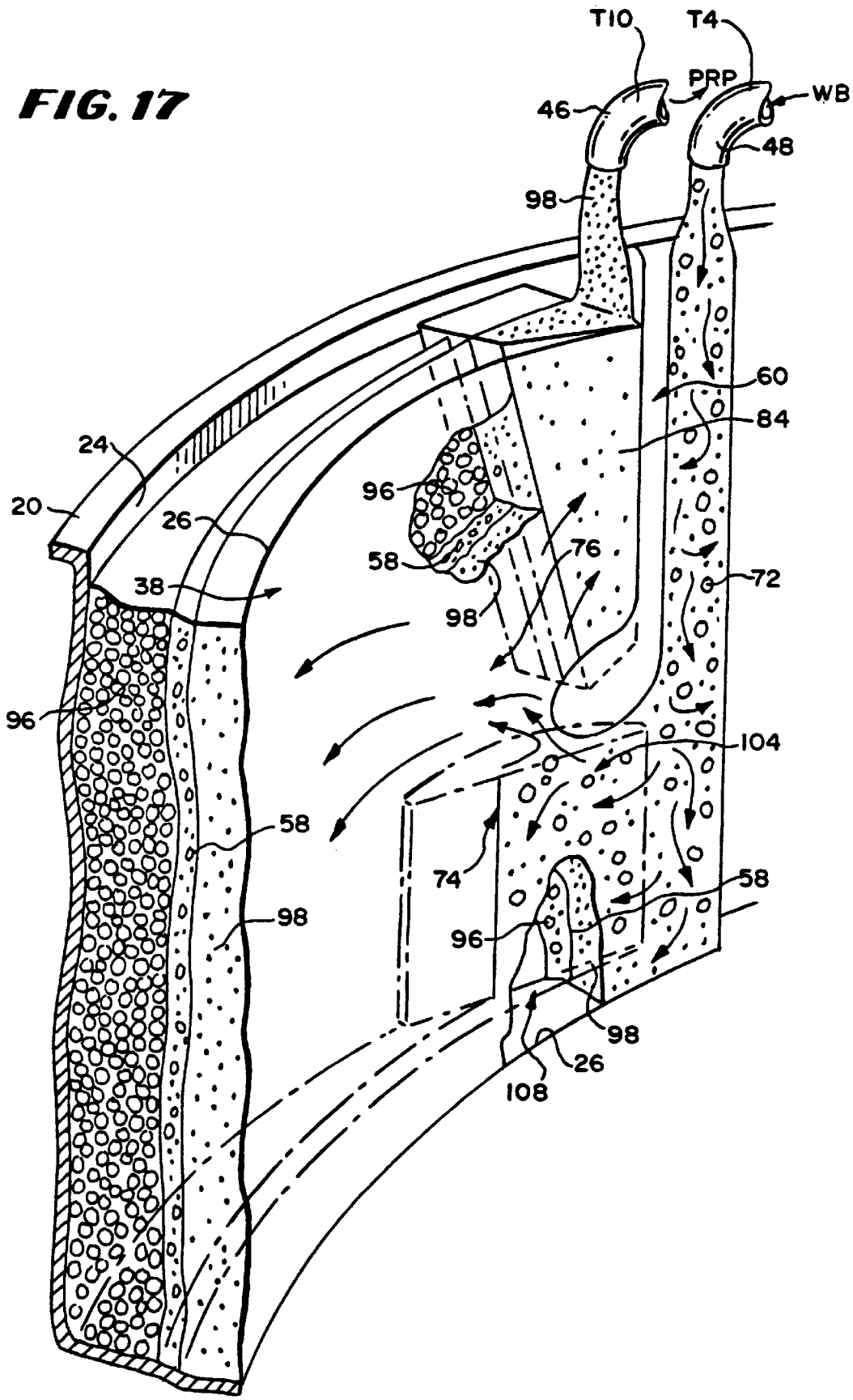
FIG. 17 is a somewhat diagrammatic view of the interior of the processing chamber, looking from the low-G wall toward the high-G wall in the region where whole blood enters the processing chamber for separation into red blood cells and platelet-rich plasma, and where platelet-rich plasma is collected in the processing chamber.

As FIG. 17 shows, WB separates in the centrifugal field within the blood processing compartment 38 into packed red blood cells (PRBC, designated by numeral 96), which move toward the high-G wall 24, and platelet-rich plasma (PRP, designated by numeral 98), which are displaced by movement of the PRBC 96 toward the low-G wall 26. An intermediate layer, called the interface (designed by numeral 58), forms between the PRBC 96 and PRP 98.

Referring back to FIG. 4, the interior seal 60 also creates a PRP collection region 76 within the blood processing compartment 38. As FIG. 17 further shows, the PRP collection region 76 is adjacent to the WB entry region 74. The velocity at which the PRBC 96 settle toward the high-G wall 24 in response to centrifugal force is greatest in the WB entry region 74 than elsewhere in the blood processing compartment 38. There is also relatively more plasma volume to displace toward the low-G wall 26 in the WB entry region 74. As a result, relatively large radial plasma velocities toward the low-G wall 26 occur in the WB entry region 74. These large radial velocities toward the low-G wall 26 elute large numbers of platelets from the PRBC 96 into the close-by PRP collection region 76.

As FIG. 4 shows, the interior seal 66 also forms a dog-leg 70 that defines a PRBC collection passage 78. A stepped-up barrier 115 (see FIG. 15) extends into the PRBC mass along the high-G wall 24, creating a restricted passage 114 between it and the facing, iso-radial high-G wall 24. The restricted passage 114 allows PRBC 96 present along the high-G wall 24 to move beyond the barrier 115 into the PRBC collection region 50, for conveyance by the PRBC collection passage 78 to the PRBC port 50. Simultaneously, the stepped-up barrier 115 blocks the passage of the PRP 98 beyond it.

Figure 15:
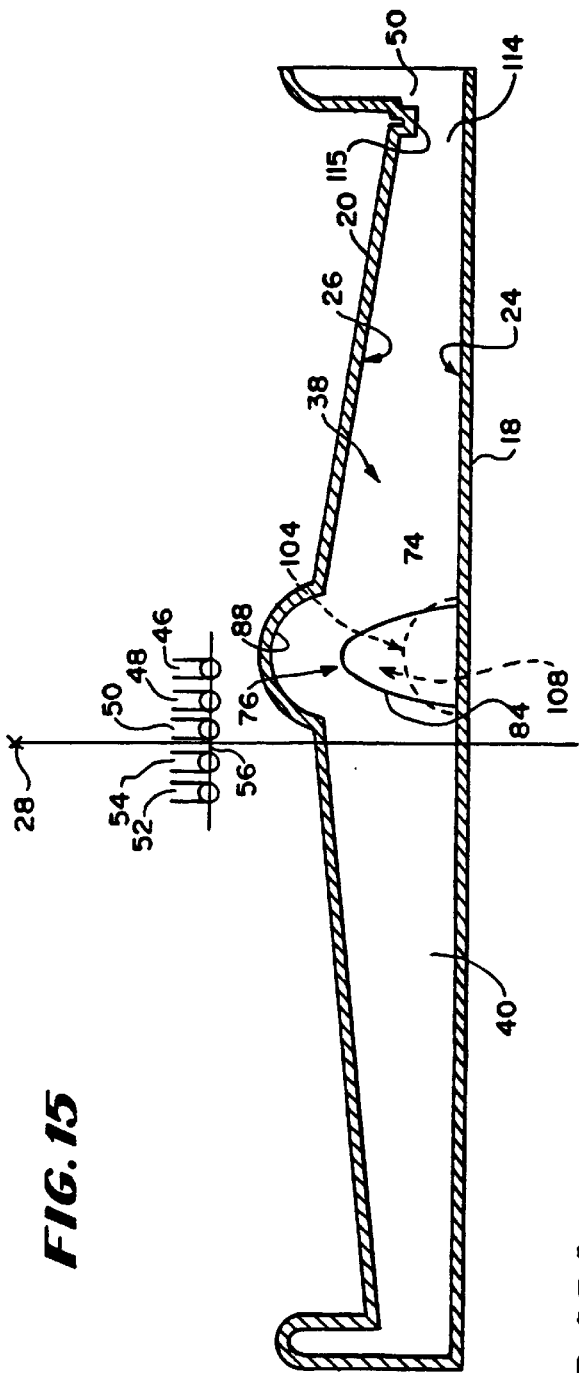
FIG. 15 is a diagrammatic top view of the separation chamber of the centrifuge shown in FIG. 1, laid out to show the radial contours of the high-G and low-G walls.
Figure 16B:
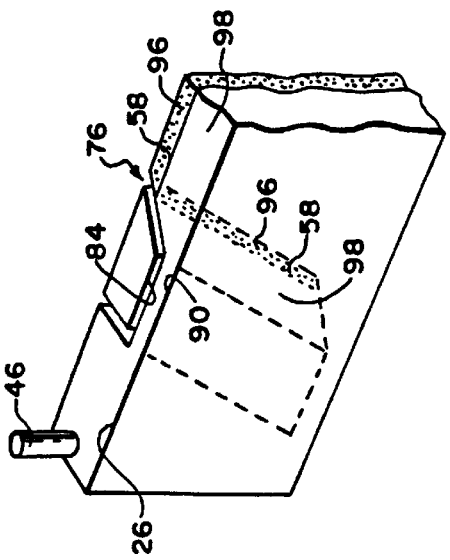
FIGS. 16A and 16B somewhat diagrammatically show a portion of the platelet-rich plasma collection zone in the separation chamber, in which the high-G wall surface forms a tapered wedge for containing and controlling the position of the interface between the red blood cells and platelet-rich plasma.
Figure 16A:
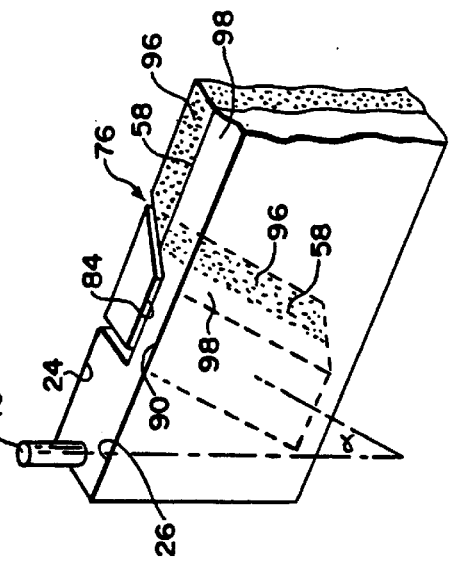

As FIGS. 15, 16A and 16B show, the high-G wall 24 also projects toward the low-G wall 26 to form a tapered ramp 84 in the PRP collection region 76. The ramp 84 forms a constricted passage 90 along the low-G wall 26, along which the PRP 98 layer extends. The ramp 84 keeps the interface 58 and PRBC 96 away from the PRP collection port 46, while allowing PRP 98 to reach the PRP collection port 46.

In the illustrated and preferred embodiment (see FIG. 16A), the ramp 84 is oriented at a non-parallel angle α of less than 45° (and preferably about 30°) with respect to the axis of the PRP port 46. The angle a mediates spill-over of the interface and PRBC through the constricted passage 90.

Figure 19:
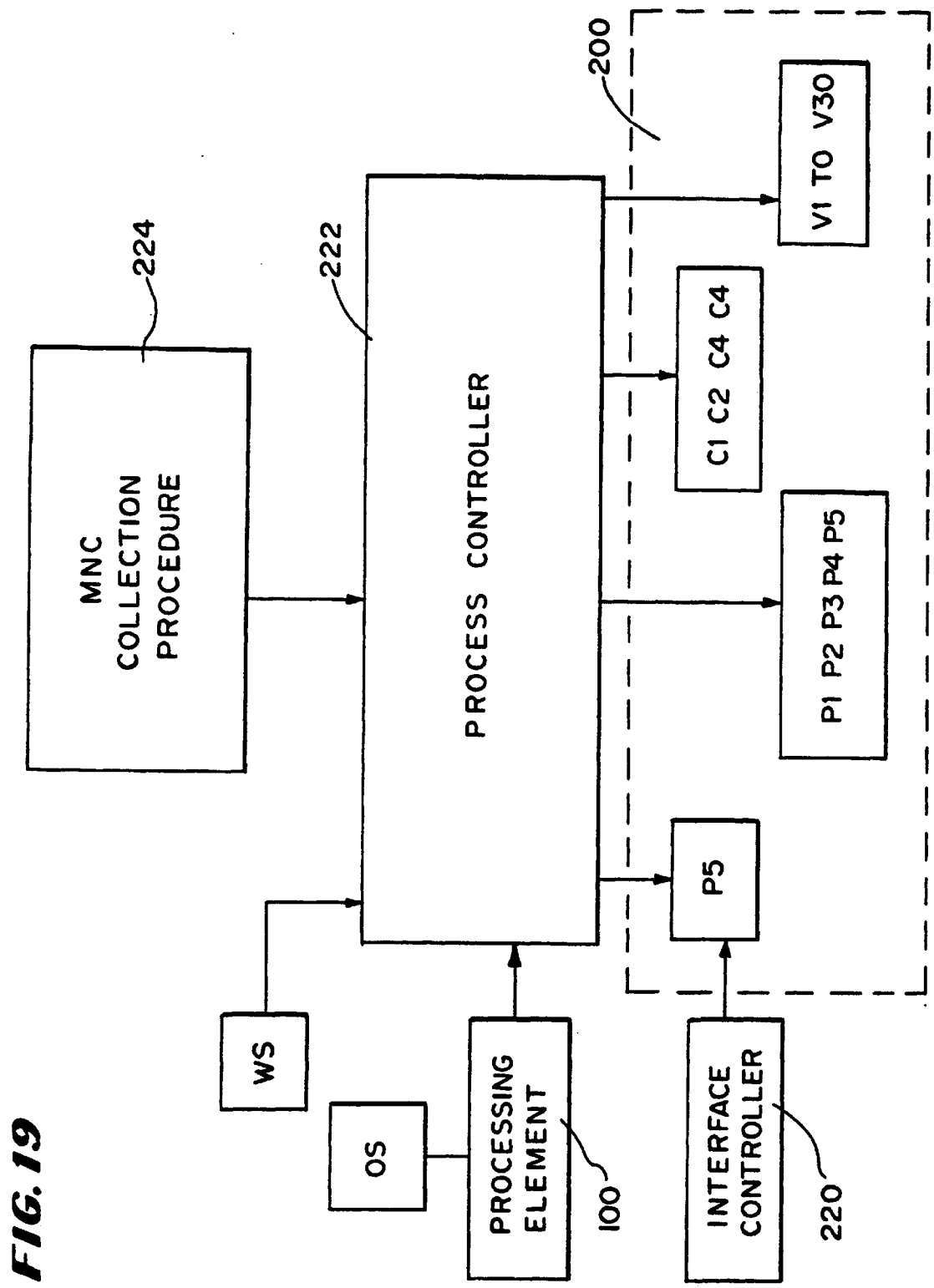
FIG. 19 is a schematic view of the process controller which configures the fluid circuit shown in FIG. 6 to conduct a prescribed MNC collection procedure.

As FIGS. 16A and 16B show, the ramp 84 also displays the interface 26 for viewing through a side wall of the container 14 by an associated interface controller 220 (see FIG. 19). The interface controller 220 controls the relative flow rates of WB, the PRBC, and the PRP through their respective ports 48, 50, and 46. In this way, the controller 220 can maintain the interface 58 at prescribed locations on ramp, either close to the constricted passage 90 (as FIG. 16A shows). or spaced away from the constricted passage 90 (as FIG. 16B shows).

By controlling the position of the interface 58 on the ramp 84 relative to the constricted passage 90, the controller 220 can also control the platelet content of the plasma collected through the port 46. The concentration of platelets in the plasma increases with proximity to the interface 58. By maintaining the interface 58 at a relatively low position on the ramp 84 (as FIG. 16B shows), the platelet-rich region is kept away from the port 46, and the plasma conveyed by the port 46 has a relatively low platelet content. By maintaining the interface 58 at a high position on the ramp 84 (as FIG. 16A shows), closer to the port 46, the plasma conveyed by the port 46 is platelet-rich.

Alternatively, or in combination, the controller could control the location of the interface 58 by varying the rate at which WB is introduced into the blood processing compartment 38, or the rate at which PRBC are conveyed from the blood processing compartment 134, or both.

Further details of a preferred embodiment for the interface controller are described in U.S. Pat. No. 5,316,667, which is incorporated herein by reference.

As FIG. 15 shows, radially opposed surfaces 88 and 104 form a flow-restricting region 108 along the high-G wall 24 of the WB entry region 74. As FIG. 17 also shows, the region 108 restricts WB flow in the WB entry region 74 to a reduced passage, thereby causing more uniform perfusion of WB into the blood processing compartment 38 along the low-G wall 26. This uniform perfusion of WB occurs adjacent to the PRP collection region 76 and in a plane that is approximately the same as the plane in which the preferred, controlled position of the interface 58 lies. Once beyond the constricted region 108 of the zone dam 104, the PRBC 96 rapidly move toward the high-G wall 24 in response to centrifugal force.

The constricted region 108 brings WB into the entry region 74 at approximately the preferred, controlled height of the interface 58. WB brought into the entry region 74 below or above the controlled height of the interface 58 will immediately seek the interface height and, in so doing, oscillate about it, causing unwanted secondary flows and perturbations along the interface 58. By bringing the WB into the entry region 74 approximately at interface level, the region 108 reduces the incidence of secondary flows and perturbations along the interface 58.

As FIG. 15 shows, the low-G wall 26 tapers outward away from the axis of rotation 28 toward the high-G wall 24 in the direction of WB flow, while the facing high-G wall 24 retains a constant radius. The taper can be continuous (as FIG. 15 shows) or can occur in step fashion. These contours along the high-G and low-G walls 24 and 26 produces a dynamic circumferential plasma flow condition generally transverse the centrifugal force field in the direction of the PRP collection region 76. As depicted schematically in FIG. 18, the circumferential plasma flow condition in this direction (arrow 214) continuously drags the interface 58 back toward the PRP collection region 76, where the higher radial plasma flow conditions already described exist to sweep even more platelets off the interface 58. Simultaneously, the counterflow patterns serve to circulate the other heavier components of the interface 58 (the lymphocytes, monocytes, and granulocytes) back into the PRBC mass, away from the PRP stream.

Within this dynamic circumferential plasma flow condition, MNC (designated as such in FIG. 18) initially settle along the high-G wall 24, but eventually float up to the surface of the interface 58 near the high-hematocrit PRBC collection region 50. The tapering low-G wall creates the plasma counterflow patterns, shown by arrows 214 in FIG. 18. These counterflow patterns 214 draw the MNC back toward the low-hematocrit PRP collection region 76. MNC again resettle near the low-hematocrit PRP collection region 76 toward the high-G wall 24.

Figure 18:
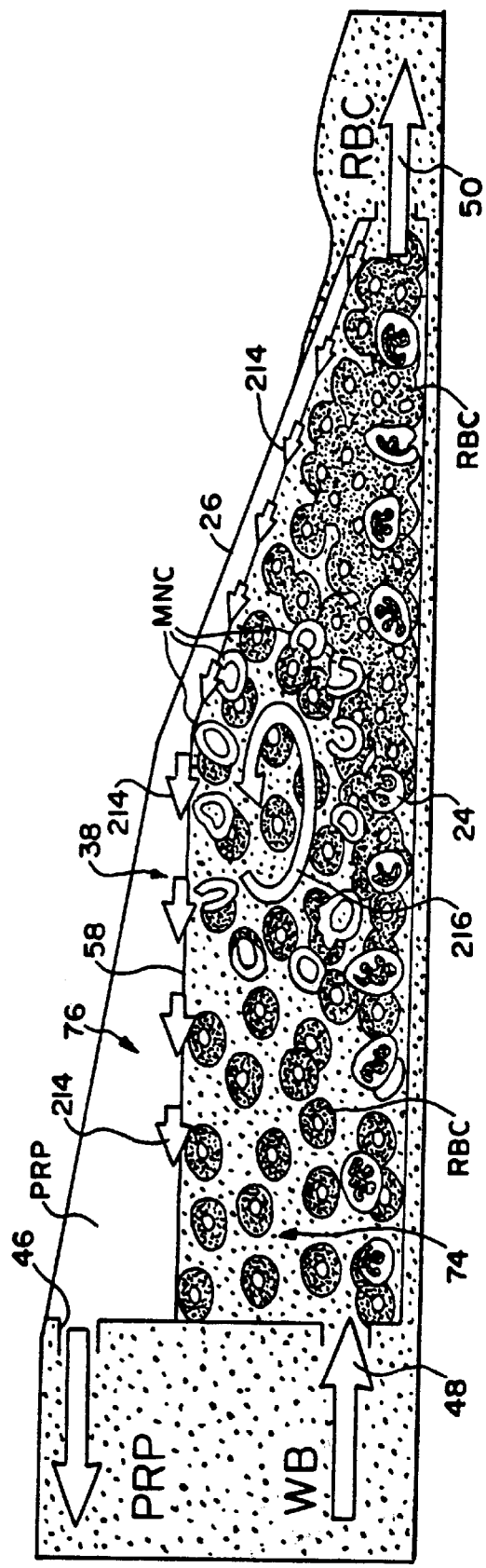
FIG. 18 is a diagrammatic view showing the dynamic flow conditions established that confine and "park" MNC within the blood separation chamber shown in FIG. 17.

The MNC circulate in this path, designated 216 in FIG. 18, while WB is separated into PRBC and PRP. The MNC are thus collected and "parked" in this confined path 216 within the compartment 38 away from both the PRBC collection region 50 and the PRP collection region 76.

Further details of the dynamics of separation in the processing compartment 38 are found in U. S. Pat. No. 5,573,678, which is incorporated herein by reference.

V. Mononuclear Cell Processing Procedure

The centrifuge 10 includes a process controller 222 (see FIG. 19), which commands operation of the fluid circuit 200 to carry out a prescribed MNC collection and harvesting procedure 224 using the container 14.

As FIG. 20 shows, the procedure 224 comprises a preprocessing priming cycle 226, which primes the fluid circuit 200. The procedure 224 next includes a preliminary processing cycle 228, which processes PPP from whole blood obtained from the donor/patient for use later in the procedure 224 as a suspension medium for the harvested MNC. The procedure 224 next includes at least one main processing cycle 230. The main processing cycle 230 comprises a collection stage 232, followed by a harvesting stage 234.

The collection stage 232 includes a series of collection phases 236 and 238, during which whole blood is processed to accumulate mononuclear cells in the first compartment 38, in the manner previously described.

The harvesting stage likewise includes a series of harvesting phases 240, 242, 244, and 246, during which the accumulation of mononuclear cells are transferred from the first compartment 38 into a collection container MNC coupled to the circuit 200. Suspension medium, collected during the preliminary processing cycle 228, is added to the MNC.

Usually, the main processing cycle 230 will be carried out more than once during a given procedure 224. The number of processing cycles 230 conducted in a given procedure 224 will depend upon the total volume of MNC sought to be collected.

For example, in a representative procedure 224, five main processing cycles 230 are repeated, one after the other. During each main processing cycle 230, from about 1500 to about 3000 ml of whole blood can be processed, to obtain a MNC volume per cycle of about 3 ml. At the end of the five processing cycles 230, a MNC volume of about 15 ml can be collected, which is suspended in a final dilution PPP of about 200 ml.

A. Pre-Processing Priming/Ballast Sequence

Before a donor/patient is coupled to the fluid circuit 200 (via tubing T1 and T9), the controller 222 conducts a priming cycle 228. During the priming cycle 228, the controller 222 commands the centrifuge 10 to rotate the spool and bowl elements 18 and 20 about the axis 28, while commanding the pumps P1 to P6 to convey a sterile priming liquid, such as saline, from the container PRIME and anticoagulant from the container ACD throughout the entire fluid circuit 15 and container 14. The priming liquid displaces air from the circuit 15 and container 14.

The second compartment 40 is served by single tubing T18 and therefore has, in effect, a single access port. To accomplish priming, the compartment 40 is isolated from flow communication with the priming liquid, while pump P5 is operated to draw air from the compartment 40, thereby creating a negative pressure (vacuum) condition in the compartment 40. Upon removal of air from the compartment 40, communication is then opened to the flow of priming liquid, which is drawn into the compartment 40 by the vacuum. Pump P5 is also operated to aid in the conveyance of liquid into the compartment 40 and to create a positive pressure condition in the compartment 40. The controller 222 retains priming liquid in the second compartment 40, to counter-balance the first compartment 38 during blood processing.

It should, of course, be appreciated that this vacuum priming procedure is applicable to the priming of virtually any container serviced by a single access port or its equivalent.

B. Preliminary Processing Cycle MNC that is harvested in container MNC is preferably suspended in a platelet-poor plasma (PPP) media obtained from the MNC donor/patient. During the preliminary processing cycle 228, the controller 222 configures the fluid circuit 222 to collect a preestablished volume of PPP from the donor/patient for retention in the container PPP. This volume is later used as a suspension medium for the MNC during processing, as well as added to the MNC after processing to achieve the desired final dilution volume.

Once the donor/patient has been phlebotomized, the controller 222 configures the pump stations PSL, PSM, and PSR to begin the preliminary processing cycle 228. During this cycle 228, whole blood is centrifugally separated in the compartment 38 into packed red blood cells (PRBC) and platelet-rich plasma (PRP), as before described. PRBC are returned to the donor/patient, while mononuclear cells accumulate in the compartment 38.

As MNC accumulate in the compartment 38, a portion of the separated plasma component is removed and collected for use as a MNC suspension medium. During this cycle 228, the controller 222 maintains the interface 58 at a relatively low position on the ramp 84 (as depicted in FIG. 16B). As a result, plasma that is conveyed from the compartment 38 and stored in the container PPP is relatively poor in platelets, and can thus be characterized as PPP. The remainder of the PPP conveyed from the compartment 38 is returned to the donor/patient during this cycle 228.

Figure 21:
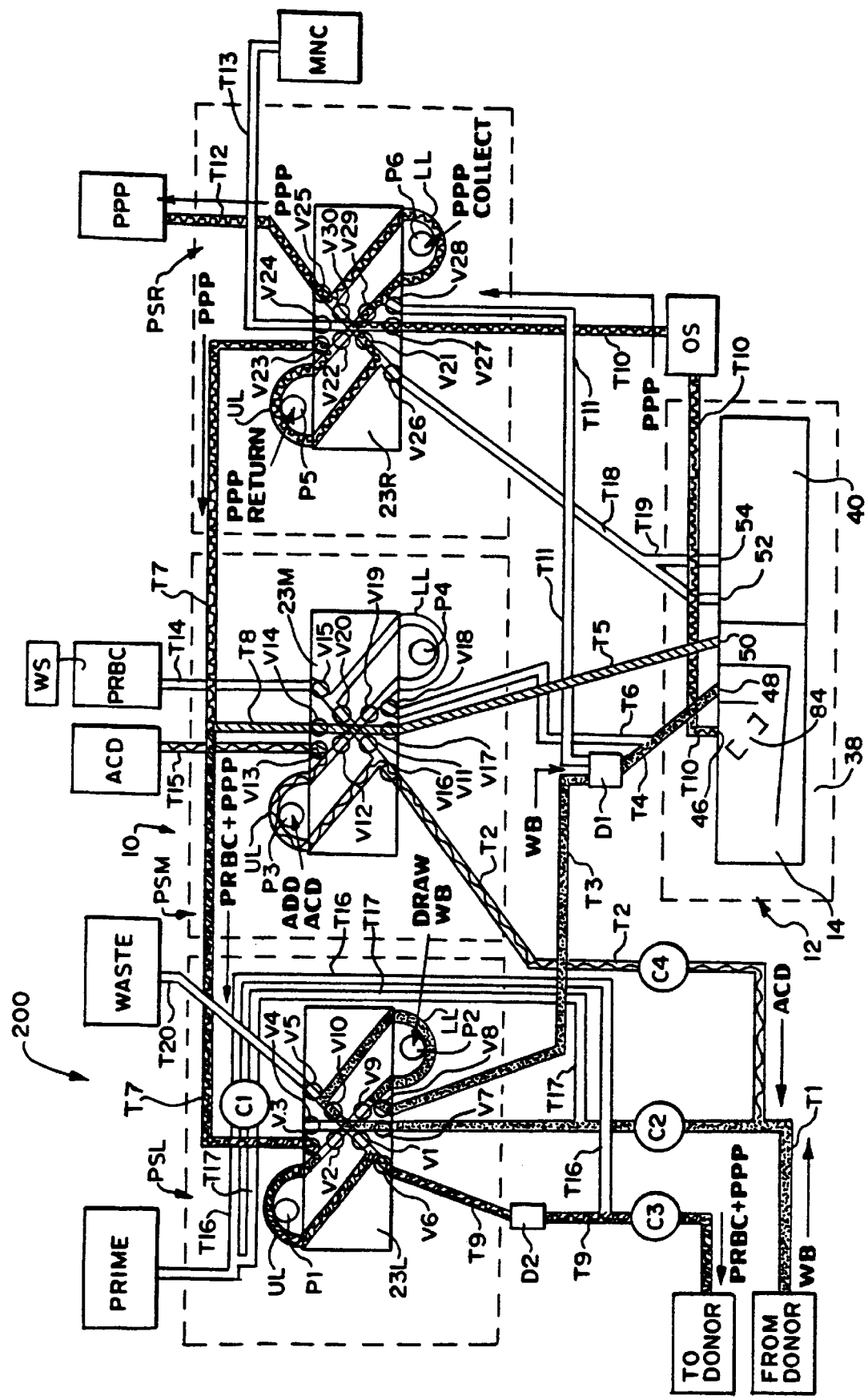
FIG. 21 is a schematic view showing the conveyance of blood components and fluids in the circuit shown in FIG. 6 during the preliminary processing cycle of the procedure shown in FIG. 20.

The configuration of the fluid circuit 200 during the preliminary processing cycle 228 is shown in FIG. 21, and is further summarized in

TABLE 2

| Preliminary Processing Cycle | | | | | | | | | | |
|---|---|---|---|---|---|---|---|---|---|---|
| V1 | • | V9 | • | V17 | o | V25 | o | C1 | • | P1 | ▣ |
| | | | | | | | | | | | o |
| V2 | • | V10 | o | V18 | • | V26 | • | C2 | o | P2 | ▶ |
| V3 | o | V11 | • | V19 | • | V27 | o | C3 | o | P3 | ▶ |
| V4 | • | V12 | • | V20 | • | V28 | • | C4 | o | P4 | ▣ |
| | | | | | | | | | | | • |
| V5 | • | V13 | o | V21 | o | V29 | o | | | P5 | ▶ |
| V6 | o | V14 | o | V22 | • | V30 | • | | | P6 | ▶ |
| V7 | o | V15 | • | V23 | o | | | | | | |
| V8 | o | V16 | o | V24 | • | | | | | | |

Where:
• indicates a tubing occluded or closed condition.
o indicates a tubing non-occluded or opened condition.
▶ indicates a pump on condition, during which the pump rotors rotate and engage the pump tubing to convey fluid in a peristaltic fashion.
▣ o indicates an opened, pump off condition, during which the pump rotors are not rotating and in which the pump rotors do not engage the pump tubing loop, and therefore permit fluid flow through the pump tubing loop.
▣ • indicates a closed, pump off condition, during which the pump rotors are not rotating, and in which the pump rotors do engage with pump tubing loop, and therefore do not permit fluid flow through the pump tubing loop.

During the preliminary cycle 228, pump P2 draws whole blood (WB) from the donor/patient through tubing T1 into the left cassette 23L, into tubing T3, through the chamber D1, and into the blood processing compartment 38 through tubing T4. Pump P3 draws anticoagulant ACD through tubing T15, into the middle cassette 23M and into tubing T2, for mixing with the whole blood.

The anticoagulated whole blood is conveyed into the compartment 38 through port 48. The whole blood is separated into PRP, PRBC, and the interface (including MNC), as previously described.

The port 50 conveys PRBC 96 from the blood processing compartment 38, through tubing T5 into the middle cassette 23M. The PRBC enters tubing T7 through tubing T8, for return to the donor/patient via the left cassette 23L and tubing T9.

The port 46 conveys PPP from the blood processing compartment 38. The PPP follows tubing T10 into the right cassette 23R. Pump P5 conveys a portion of the PPP into tubing T7 for return with PRBC to the donor/patient. The interface controller 220 sets the flow rate of pump P5 to maintain the interface at a low position on the ramp 84 (as shown in FIG. 16B), to thereby minimize the concentration of platelets conveyed from the compartment 38 during this cycle. Pump P6 conveys a portion of the PPP through tubing T12 into container PPP, until the volume prescribed for MNC suspension and final dilution is collected. This volume is designated $VOL_{sus}$.

C. Main Processing Cycle

1. Mononuclear Cell (MNC) Collection Stage (i) MNC Accumulation Phase

The controller 222 now switches to the MNC collect stage 232 of the main processing cycle 230. First, the controller 222 configures the fluid circuit 200 for the MNC accumulation phase 236.

For the phase 236, the controller 222 changes the configuration of the pump station PSR to stop collection of PPP.

The controller 222 also commands the interface controller 220 to maintain a flow rate for pump P5 to maintain the interface at a higher location on the ramp 84 (such as shown in FIG. 16A), thereby enabling the separation of PRP.

Due to the changed configuration, the pump P6 also recirculates a portion of the PRP to the blood processing chamber 38 to enhance platelet separation efficiencies, as will be described in greater detail later.

Figure 22:
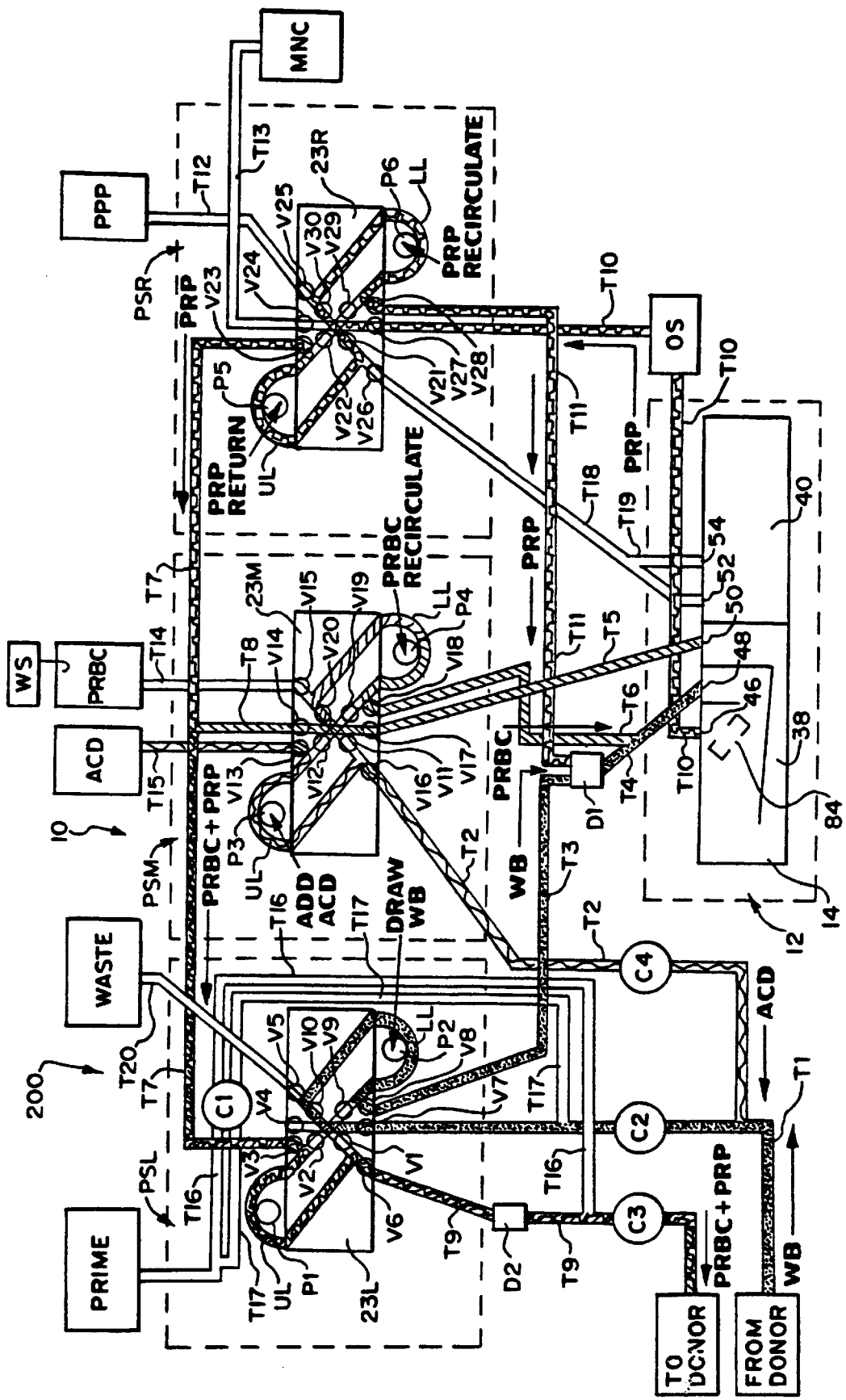
FIG. 22 is a schematic view showing the conveyance of blood components and fluids in the circuit shown in FIG. 6 during the MNC accumulation phase of the procedure shown in FIG. 20.

The configuration for the MNC accumulation phase 236 of the MNC collect stage 232 is shown in FIG. 22, and is further summarized in Table 3.

TABLE 3

Mononuclear Cell Collect Condition
(MNC Accumulation Phase)

| V1 | • | V9  | • | V17 | ○ | V25 | • | C1 | • | P1 | ▣ |
|----|---|-----|---|-----|---|-----|---|----|---|----|---|
|    |   |     |   |     |   |     |   |    |   |    | ○ |
| V2 | • | V10 | ○ | V18 | ○ | V26 | • | C2 | ○ | P2 | ▶ |
| V3 | ○ | V11 | • | V19 | • | V27 | ○ | C3 | ○ | P3 | ▶ |
| V4 | • | V12 | • | V20 | ○ | V28 | ○ | C4 | ○ | P4 | ▶ |
| V5 | • | V13 | ○ | V21 | ○ | V29 | • |    |   | P5 | ▶ |
| V6 | ○ | V14 | ○ | V22 | • | V30 | ○ |    |   | P6 | ▶ |
| V7 | ○ | V15 | • | V23 | ○ |     |   |    |   |    |   |
| V8 | ○ | V16 | ○ | V24 | • |     |   |    |   |    |   |

Where:
• indicates a tubing occluded or closed condition.
○ indicates a tubing non-occluded or opened condition.
▶ indicates a pump on condition, during which the pump rotors rotate and engage the pump tubing to convey fluid in a peristaltic fashion.
▣ ○ indicates an opened, pump off condition, during which the pump rotors are not rotating and in which the pump rotors do not engage the pump tubing loop, and therefore permit fluid flow through the pump tubing loop.
▣ • indicates a closed, pump off condition, during which the pump rotors are not rotating, and in which the pump rotors do engage with pump tubing loop, and therefore do not permit fluid flow through the pump tubing loop.

1. Promoting High Platelet Separation Efficiencies By Recirculation of PRP

Normally, platelets are not collected during a MNC procedure. Instead, it is believed desirable to return them to the donor/patient. A high mean platelet volume MPV (expressed in femtoliters, fl, or cubic microns) for separated platelets is desirable, as it denotes a high platelet separation efficiency. MPV can be measured by conventional techniques from a PRP sample. Larger platelets (i.e., larger than about 20 femtoliters) are most likely to become entrapped in the interface 58 and not enter the PRP for return to the donor/patient. This results in a reduced population of larger platelets in the PRP, and therefore a lower MPV, for return to the donor/patient.

The establishment of radial plasma flow conditions sufficient to lift larger platelets from the interface 58, as previously described, is highly dependent upon the inlet hematocrit $H_i$ of WB entering the blood processing compartment 38. For this reason, the pump 6 recirculates a portion of the PRP flowing in tubing T10 back into the WB inlet port 48. The recirculating PRP flows through the right cassette 23R into tubing T11, which joins tubing T4 coupled to the inlet port 48. The recirculating PRP mixes with WB entering the blood processing compartment 38, thereby lowering inlet hematocrit $H_i$.

The controller sets a PRP recirculation flow rate $Q_{Recirc}$ for pump P6 to achieve a desired inlet hematocrit $H_i$. In a preferred implementation, $H_i$ is no greater that about 40%, and, most preferably, is about 32%, which will achieve a high MPV.

Inlet hematocrit $H_i$ can be conventionally measured by an in-line sensor in tubing T4 (not shown). Inlet hematocrit $H_i$ can also be determined empirically based upon sensed flow conditions, as disclosed in copending U. S. patent application Ser. No. 08/471,883, now U. S. Pat. No. 5,641,414 which is incorporated herein by reference.

2. Promoting High MNC Concentration and Purity By Recirculation of PRBC

As depicted schematically in FIG. 18, the counter flow of plasma (arrows 214) in the compartment 38 drags the interface 58 back toward the PRP collection region 76, where the enhanced radial plasma flow conditions sweep platelets off the interface 58 for return to the donor/patient. The counterflow patterns 214 also circulate other heavier components of the interface 58, such as lymphocytes, monocytes, and granulocytes, back for circulation into the PRBC mass.

Meanwhile, due to the relatively high hematocrit in the PRBC collection region 80, MNC float near the region 80 to the surface of the interface 58. There, the MNC are drawn by the plasma counter-flow 214 toward the low-hematocrit PRP collection region 76. Due to the lower hematocrit in this region 76, MNC resettle again toward the high-G wall 24. Arrow 216 in FIG. 18 shows the desired circulating flow of MNC as it accumulates in the compartment 38.

Maintaining a desired PRBC outlet hematocrit $H_o$ in the PRBC collection region 50 is important. If the outlet hematocrit $H_o$ of the PRBC falls below a given low threshold value (e.g., below about 60%), the majority of MNC will not circulate as a cellular mass, as shown by the arrow 216 in FIG. 18. Exposed to a low $H_o$, all or some of the MNC will fail to float toward the interface 58. Instead, the MNC will remain congregated along the high-G wall and will be carried out of the compartment 38 with the PRBC. An insufficient MNC yield results.

On the other hand, if $H_o$ exceeds a given high threshold value (e.g., about 85%), larger numbers of the heavier granulocytes will float on the interface 58. As a result, fewer granulocytes will be carried away from the interface 58 for return with the PRBC to the donor/patient. Instead, more granulocytes will occupy the interface 58 and contaminate the MNC.

For this reason, during the MNC collection stage 232, the process controller 222 commands the pump P4 to recirculate a portion of the PRBC flowing in tubing T5 back into the WB inlet port 48. As FIGS. 21 and 22 show, recirculating PRBC flows through the middle cassette 23M into tubing T6, which joins tubing T4 coupled to the inlet port 48. The recirculating PRBC mixes with WB entering the blood processing compartment 38.

Generally speaking, the magnitude of the outlet hematocrit $H_o$ varies conversely as a function of PRBC recirculation flow rate $Q_r$, which is governed by the pump P4 (PRBC) and the pump P2 (WB). Given a flow rate for WB set by pump P2, the outlet hematocrit H. can be increased by lowering $Q_r$, and, conversely, outlet hematocrit $H_o$ can be decreased by raising $Q_r$. The exact relationship between $Q_r$ and $H_o$ takes into account the centrifugal acceleration of fluid in the compartment 38 (governed by the magnitude of centrifugal forces in the compartment 38), the area of the compartment 38, as well as the inlet flow rate whole blood ($Q_b$) into the compartment 38 (governed by pump P2) and the outlet flow rate PRP ($Q_p$) from the compartment 38 (governed by the interface control pump P5).

There are various ways of expressing this relationship and thereby quantifying $Q_r$ based upon a desired $H_o$. In the illustrated embodiment, the controller 222 periodically samples $Q_b$, $Q_p$, and $Q_r$. Further taking into account the centrifugal force factors active in the compartment 38, the controller derives a new PRBC recirculation pump rate $Q_r$ (NEW) for the pump P4, based upon a targeted $H_o$, as follows:

(i) Start at sample time n=0
(ii) Calculate current $Q_r$ as follows:

$$Q_r = [Q_p - Q_b] + \left[\frac{k}{H_o} - 1\right]\left[\frac{a*A}{m}\right]$$

where:
$H_o$ is the targeted exit hematocrit value, expressed as a decimal (e.g., 0.75 for 75%).
a is the acceleration of fluid, governed by centrifugal forces, calculated at follows:

$$a = \frac{r\Omega^2}{g}$$

where:
$\Omega$ is the rate of rotation of the compartment 38, expressed in radians per second.
r is the radius of rotation.
g is unit gravity, equal to 981 cm/sec$^2$.
A is the area of the compartment 38.
k is hematocrit constant and m is a separation performance constant, which are derived based upon empirical data and/or theoretical modeling. In the preferred embodiment, the following theoretical model is used:

$$H_o(1 - H_o)^{k\%1} = \frac{\beta Q_b H_i}{aAC_R}$$

where:

$C_R = 1.08 S_r$ and where:
$\beta$ is a shear sensitive term defined as:

$$\beta = 1 + \frac{b}{\tau^n}$$

and where:
based upon empirical data, b=6.0 s$^{-n}$ and n=0.75, and shear rate is defined as:

$\tau = du/dy$ in which (u) is the fluid velocity and (y) is a spatial dimension.
and where:
$S_r$ is an empirically derived red blood cell sedimentation factor, which, upon empirical data, can be set at 95×10$_{-9}$ s.

This model is based upon Equation (19) of Brown, "The Physics of Continuous Flow Centrifugal Cell Separation," *Artificial Organs*; 13(1):4–20, Raven Press, Ltd., New York (1989) (the "Brown Article"), which is incorporated herein by reference. The plot of the model appears in FIG. 9 of the Brown Article.

The above model is linearized using simple linear regression over an expected, practical operating range of blood processing conditions. Algebraic substitutions are made based upon the following expressions:

$H_i Q_b = H_o Q_o$ where:
$Q_o$ is the flow rate of PRBC through outlet tubing T5, which can be expressed as:

$Q_o = Q_b - Q_p$

This linearization yields a simplified curve in which the value of (m) constitutes the slope and the value of (k) constitutes the y-intercept.
In the simplified curve, the slope (m) is expressed as follows:

$$m = 338.3\left(\frac{\beta}{S_r}\right)$$

where:
$\beta/S_r$ can, based upon empirical data, be expressed as a constant value of 1.57$\mu$s.
Therefore, in the simplified curve, m has a value of 531.13. A range of values for m between about 500 and about 600 is believed to be applicable to centrifugal, continuous flow whole blood separation procedures, in general.

For the simplified curve, the y-intercept value for (k) equals 0.9489. A range of values for k between about 0.85 and about 1.0 is believed to be applicable to centrifugal, continuous flow whole blood separation procedures, in general.

(iii) Calculate Average $Q_r$
$Q_r$ is measured at selected intervals, and these instantaneous measurements are averaged over the processing period, as follows:

$Q_r(\text{AVG}) = [0.95(Q_r(\text{AVG}_{LAST})] + [0.05*Q_r]$ (iv) Calculate new $Q_r$, as follows:

$Q_r(\text{NEW}) = Q_r(\text{AVG})*F$ where:
F is an optional control factor, which enables the control of $Q_r$ (when F=1), or disables the control of $Q_r$ (when F=0), or enables a scaling of $Q_r$ based upon system variances (when F is expressed as a fraction between 0 and 1). F can comprise a constant or, alternatively, it can vary as a function of processing time, e.g., starting at a first value at the outset of a given procedure and changing to a second or more values as the procedure progresses.

(v) Keep $Q_r$ within prescribed limits (e.g., between 0 ml/min and 20 ml/min)
IF
   $Q_r(\text{NEW})>20$ ml/min THEN
   $Q_r(\text{NEW})=20$ ml/min
ENDIF
IF
   $Q_r(\text{NEW})<0$ ml/min THEN
   $Q_r(\text{NEW})=0$ ml/min
ENDIF
n=n+1

During the MNC collect stage 232 (FIG. 22), the controller 222 simultaneously sets and maintains multiple pump flow rates to achieve processing conditions in the compartment 38 optimal for the accumulation of a high yield of MNC of high purity. The controller sets and maintains WB inlet flow rate $Q_b$ (via the pump P2), PRP outlet flow rate $Q_p$ (via the pump P5), PRP recirculation flow rate $Q_{recirc}$ (via the pump P6), and PRBC recirculation flow rate $Q_r$ (via the pump P4). Given a WB inlet flow rate $Q_b$, which is typically set for donor/patient comfort and the achievement of an acceptable processing time, the controller 222:

(i) commands pump P5 to maintain a $Q_p$ set to hold a desired interface position on the ramp 84, and thereby achieve the desired platelet concentrations in the plasma (PPP or PRP);

(ii) commands the pump P6 to maintain a $Q_{Recirc}$ set to hold the desired inlet hematocrit $H_i$ (e.g., between about 32% and 34%), and thereby achieve high platelet separation efficiencies; and (iii) commands the pump P4 to maintain a $Q_r$ set to hold a desired outlet hematocrit $H_o$ (e.g., between about 75% to 85%), and thereby prevent granulocyte contamination and maximize MNC yields.

(ii). Second Phase (PRBC Collect)

The controller 222 terminates the MNC accumulation phase 236 when a preestablished volume of whole blood (e.g., 1500 ml to 3000 ml) is processed. Alternatively, the MNC accumulation phase can be terminated when a targeted volume of MNC is collected.

The controller 22 then enters the PRBC collection phase 238 of the MNC collection stage 232. In this phase 238, the configuration of the pump station PSM is altered to stop the return of PRBC to the donor/patient (by closing V14), stop the recirculation of PRBC (by closing valve V18 and placing pump P4 into a closed, pump off condition, and instead conveying PRBC to the container PRBC (by opening V15).

This new configuration is shown in FIG. 23, and is further summarized in Table 4.

TABLE 4

Mononuclear Cell Collect Stage
(Collect PRBC Phase)

| V1 | • | V9  | • | V17 | o | V25 | • | C1 | • | P1 | ▣ |
|    |   |     |   |     |   |     |   |    |   |    | o |
| V2 | • | V10 | o | V18 | • | V26 | • | C2 | o | P2 | ▶ |
| V3 | o | V11 | • | V19 | • | V27 | o | C3 | o | P3 | ▶ |
| V4 | • | V12 | • | V20 | o | V28 | o | C4 | o | P4 | ▣ |
|    |   |     |   |     |   |     |   |    |   |    | • |
| V5 | • | V13 | o | V21 | o | V29 | • |    |   | P5 | ▶ |
| V6 | o | V14 | • | V22 | • | V30 | • |    |   | P6 | ▶ |
| V7 | o | V15 | o | V23 | o |     |   |    |   |    |   |
| V8 | o | V16 | o | V24 | • |     |   |    |   |    |   |

Where:
• indicates a tubing occluded or closed condition.
o indicates a tubing non-occluded or opened condition.
▶ indicates a pump on condition, during which the pump rotors rotate and engage the pump tubing to convey fluid in a peristaltic fashion.
▣ o indicates an opened, pump off condition, during which the pump rotors are not rotating and in which the pump rotors do not engage the pump tubing loop, and therefore permit fluid flow through the pump tubing loop.
▣ • indicates a closed, pump off condition, during which the pump rotors are not rotating, and in which the pump rotors do engage with pump tubing loop, and therefore do not permit fluid flow through the pump tubing loop.

In this phase 238, PRBC in line T5 is conveyed through the middle cassette 23M, into line T14, and into the container PRBC. The controller 222 operates in this phase 238 until a desired volume of PRBC (e.g., 35 ml to 50 ml) collects in the container PRBC. This PRBC volume is later used in the MNC removal phase 240 of the MNC harvesting stage 234, as will be described in greater detail later.

The controller 222 ends the PRBC collection phase 238 upon sensing (gravimetrically, using the weight scale WS) that the container PRBC holds the desired volume of PRBC.

The ends the MNC collection stage 232 of the main processing cycle 230.

2. Mononuclear Cell Harvesting Stage (i) First Phase (MNC Removal)

The controller 222 enters the MNC harvesting stage 234 of the main processing cycle 230. In the first phase 240 of this stage 234, whole blood is drawn and recirculated back to the donor/patient without passage through the blood processing compartment 38. PRBC collected in the container PRBC in the preceding PRBC collection phase 238 is returned to the processing compartment 38 through WB inlet tubing T4, while rotation of the compartment 38 continues. The MNC accumulated in the compartment 38 during the MNC collection stage 232 is conveyed with PRP through tubing T10 out of the compartment 38.

The configuration of the fluid circuit 15 during the MNC removal phase 240 of the MNC harvesting stage 234 is shown in FIG. 24A, and is further summarized in Table 5:

TABLE 5

Mononuclear Cell Harvesting Stage
(MNC Removal Phase)

| V1 | • | V9  | • | V17 | o | V25 | o | C1 | • | P1 | ▶ |
|    |   |     |   |     |   | or  |   |    |   |    |   |
|    |   |     |   |     |   | •   |   |    |   |    |   |
| V2 | o | V10 | o | V18 | o | V26 | • | C2 | o | P2 | ▣ |
|    |   |     |   |     |   |     |   |    |   |    | • |
| V3 | • | V11 | • | V19 | • | V27 | o | C3 | o | P3 | ▶ |
| V4 | • | V12 | • | V20 | • | V28 | o | C4 | o | P4 | ▶ |
| V5 | • | V13 | o | V21 | o | V29 | • |    |   | P5 | ▣ |
|    |   |     |   |     |   |     |   |    |   |    | • |
| V6 | o | V14 | • | V22 | • | V30 | o |    |   | P6 | ▣ |
|    |   |     |   |     |   |     |   |    |   |    | • |
| V7 | o | V15 | o | V23 | o |     |   |    |   |    |   |
| V8 | o | V16 | o | V24 | • |     |   |    |   |    |   |

Where:
• indicates a tubing occluded or closed condition.
o indicates a tubing non-occluded or opened condition.
▶ indicates a pump on condition, during which the pump rotors rotate and engage the pump tubing to convey fluid in a peristaltic fashion.
▣ o indicates an opened, pump off condition, during which the pump rotors are not rotating and in which the pump rotors do not engage the pump tubing loop, and therefore permit fluid flow through the pump tubing loop.
▣ • indicates a closed, pump off condition, during which the pump rotors are not rotating, and in which the pump rotors do engage with pump tubing loop, and therefore do not permit fluid flow through the pump tubing loop.

As FIG. 24A shows, the controller 222 closes PRBC outlet tubing T5 while PRBC is conveyed by pump P4 from the container PRBC through tubing T14 and T6 into tubing T4, for introduction into compartment 38 through the WB inlet port 48. The controller 222 starts a cycle time counter at $TCYC_{START}$.

The inflow of PRBC from the container PRBC through the WB inlet port 48 increases the hematocrit in the PRP collection region 76. In response, the concentrated region of MNC accumulated in the compartment 38 (as shown in FIG. 18), float to the surface of the interface 58. The incoming PRBC volume displaces PRP through the PRP outlet port 46. The interface 58, and with it, the concentrated MNC region (designated MNC Region in FIG. 24A) are also displaced out of the compartment 38 through the PRP outlet port 46. The MNC Region moves along the PRP tubing T10 toward the optical sensor OS.

As FIG. 28 shows, within the tubing T10, a region 112 of PRP precedes the concentrated MNC Region. The PRP in this region 112 is conveyed into the container PPP through the right cassette 23R and tubing T12 (as FIG. 24A shows). A region 114 of PRBC also follows the concentrated MNC Region within the tubing T10.

A first transition region 116 exists between the PRP region 112 and concentrated MNC Region. The first transition region 116 consists of a steadily decreasing concentration of platelets (shown by a square pattern in FIG. 28) and a steadily increasing number of MNC's (shown by a textured pattern in FIG. 28).

A second transition region 118 exists between the concentrated MNC Region and the PRBC region 114. The second transition region 118 consists of a steadily decreasing concentration of MNC's (shown by the textured pattern in FIG. 28) and a steadily increasing number of PRBC's (shown by a wave pattern in FIG. 28).

Viewed by the optical sensor OS, the regions 112 and 116 preceding the MNC Region and the regions 118 and 114 trailing the MNC Region present a transition optical densities in which the MNC Region can be discerned. The optical sensor OS senses changes in optical density in the liquid conveyed by the tubing T10 between the PRP outlet port 46 and the right cassette 23R. As FIG. 28 shows, the optical density will change from a low value, indicating highly light transmissive (i.e., in the PRP region 112), to a high value, indicating highly light absorbent (i.e., in the PRBC region 114), as the MNC Region progresses past the optical sensor OS.

In the illustrated embodiment shown in FIG. 28, the optical sensor OS is a conventional hemoglobin detector, used, e.g., on the Autopheresis-Cs® blood processing device sold by the Fenwal Division of Baxter Healthcare Corporation. The sensor OS comprises a red light emitting diode 102, which emits light through the tubing T10. Of course, other wavelengths, like green or infrared, could be used. The sensor OS also includes a PIN diode detector 106 on the opposite side of the tubing T10.

The controller 222 includes a processing element 100, which analyzes voltage signals received from the emitter 102 and detector 106 to compute the optical transmission of the liquid in the tubing T10, which is called OPTTRANS.

Various algorithms can be used by the processing element 100 to compute OPTTRANS.

For example, OPTRANS can equal the output of the diode detector 106 when the red light emitting diode 102 is on and the liquid flows through the tubing T10 (RED).

Background optical "noise" can be filtered from RED to obtain OPTTRANS, as follows:

$$OPTTRANS = \frac{COR(RED\ SPILL)}{CORREF}$$

where COR(RED SPILL) is calculated as follows:

COR(RED SPILL)=RED−REDBKGRD where:
RED is the output of the diode detector 106 when the red light emitting diode 102 is on and the liquid flows through the tubing T10;
REDBKGRD is the output of the diode detector 106 when the red light emitting diode 102 is off and the liquid flows through the tubing T10;
and where CORREF is calculated as follows:

CORREF=REF−REFBKGRD where:
REF is the output of the red light emitting diode 102 when the diode is on; and
REFBKGRD is the output of the red light emitting diode 102 when the diode is off.

The processing element 100 normalizes the sensor OS to the optical density of the donor/patient's PRP, by obtaining data from the sensor OS during the preceding MNC collection stage 232, as the donor/patient's PRP conveys through the tubing T10. This data establishes a baseline optical transmission value for the tubing and the donor/patient's PRP (OPTTRANS$_{BASE}$). For example, OPTTRANS$_{BASE}$ can be measured at a selected time during the collection stage 232, e.g., half way through the stage 232, using either a filtered or non-filtered detection scheme, as described above. Alternatively, a set of optical transmission values are calculated during the MNC collection stage 232 using either a filtered or non-filtered detection scheme. The set of values are averaged over the entire collection stage to derive OPTTRANS$_{BASE}$.

The processing element 100 continues during the subsequent MNC removal phase 240 to sense one or more optical transmission values for the tubing T10 and the liquid flowing in it (OPTTRANS$_{HARVEST}$) during the MNC removal phase 240. OPTTRANS$_{HARVEST}$ can comprise a single reading sensed at a selected time of the MNC removal phase 240 (e.g., midway through the phase 240), or it can comprise an average of multiple readings taken during the MNC removal phase 240.

The processing element 100 derives a normalized value DENSITY by establishing OPTTRANS$_{BASE}$ as 0.0, establishing the optical saturation value as 1.0, and fitting the value of OPTTRANS$_{HARVEST}$ proportionally into the normalized 0.0 to 1.0 value range.

As FIG. 28 shows, the processing element 100 retains two predetermined threshold values THRESH(1) and THRESH(2). The value of THRESH(1) corresponds to a selected nominal value for DENSITY (e.g., 0.45 in a normalized scale of 0.0 to 1.0), which has been empirically determined to occur when the concentration of MNC's in the first transition region 116 meets a preselected processing goal. The value of THRESH(2) corresponds to another selected nominal value for DENSITY (e.g., 0.85 in a normalized scale of 0.0 to 1.0), which has been empirically determined to occur when the concentration of PRBC in the second transition region 118 exceeds the preselected processing goal.

The liquid volume of the tubing T10 between the optical sensor OS and the valve station V24 in the right cassette 23R constitutes a known value, which is inputted to the controller 222 as a first offset volume VOL$_{OFF(1)}$. The controller 222 calculates a first control time value Time$_1$ based upon VOL$_{OFF(1)}$ and the pump rate of pump P4 (Q$_{P4}$), as follows:

$$Time_1 = \frac{VOL_{OFF(1)}}{Q_{P4}} \times 60$$

In the illustrated and preferred embodiment, the operator can specify and input to the controller 222 a second offset volume VOL$_{OFF(2)}$, which represents a nominal additional volume (shown in FIG. 28) to increase the total MNC harvested volume VOL$_{MNC}$. The quantity VOL$_{OFF(2)}$ takes into account system and processing variances, as well as variances among donors/patients in MNC purity. The controller 222 calculates a second control time value Time$_2$ based upon VOL$_{OFF(2)}$ and the pump rate of pump P4 (Q$_{P4}$), as follows:

$$Time_2 = \frac{VOL_{OFF(2)}}{Q_{P4}} \times 60$$

As operation of the pump P4 conveys PRBC through the WB inlet port 48, the interface 58 and MNC Region advance through the PRP tubing T10 toward the optical sensor OS. PRP preceding the MNC Region advances beyond the optical sensor OD, through the tubing T12, and into the container PPP.

When the MNC Region reaches the optical sensor OS, the sensor OS will sense DENSITY=THRESH(1). Upon this event, the controller 222 starts a first time counter $TC_1$. When the optical sensor OS senses DENSITY=THRESH(2) the controller 222 starts a second time counter $TC_2$ The volume of MNC sensed can be derived based upon the interval between $TC_1$ and $TC_2$ for a given $Q_{P4}$.

As time advances, the controller 222 compares the magnitudes of $TC_1$ to the first control time $T_1$, as well as compares $TC_2$ to the second control time $T_2$. When $TC_1=T_1$, the leading edge of the targeted MNC Region has arrived at the valve station V24, as FIG. 24B shows. The controller 222 commands valve station V24 to open, and commands valve station V25 to close. The controller 222 marks this event on the cycle time counter as $TCYC_{SWITCH}$. The targeted MNC Region is conveyed into the tubing T13 that leads to the container MNC. When $TC_2=T_2$, the second offset volume $VOL_{OFF(2)}$ has also been conveyed into the tubing T13, as FIG. 24C shows. The total MNC volume selected for harvesting ($VOL_{MNC}$) for the given cycle is thereby present in the tubing T13. When $TC_2=T_2$, the controller 222 commands the pump P4 to stop. Further advancement of $VOL_{MNC}$ in the tubing T13 therefore ceases.

The controller 222 derives the volume of PRP that was conveyed into the container PPP during the preceding MNC removal phase. This PRP volume (which is designated $VOL_{PRP}$) is derived, as follows:

$$VOL_{PRP} = \frac{TCYC_{SWITCH} - TCYC_{START}}{Q_4}$$

In a preferred embodiment, the controller 222 ends the MNC removal phase, independent of $TC_1$ and $TC_2$ when the pump P4 conveys more than a specified fluid volume of PRBC after $TCYC_{START}$ (e.g., more than 60 ml). This time-out circumstance could occur, e.g., if the optical sensor OS fails to detect THRESH(1). In this volumetric time-out circumstance, $VOL_{PRP}=60-VOL_{OFF(1)}$.

Alternatively, or in combination with a volumetric time-out, the controller 222 can end the MNC removal phase independent of $TC_1$ and $TC_2$ when the weight scale WS for the container PRBC senses a weight less than a prescribed value (e.g., less than 4 grams, or the weight equivalent of a fluid volume less than 4 ml).

(ii) Second Phase (PRP Flush)

Once the MNC Region is positioned as shown in FIG. 24C, the controller 222 enters the PRP flush phase 242 of the MNC harvesting stage 234. During this phase 242, the controller 222 configures the circuit 200 to move $VOL_{PRP}$ out of the container PPP and tubing T12 and into the blood processing compartment 38.

The configuration of the fluid circuit 200 during the PRP flush phase 242 is shown in FIG. 25, and is further summarized in Table 6.

TABLE 6

Mononuclear Cell Harvesting Stage
(PRP Flush Phase)

| V1 | • | V9  | • | V17 | ○ | V25 | ○ | C1 | • | P1 | ■ |
|    |   |     |   |     |   |     |   |    |   |    | ○ |
| V2 | • | V10 | ○ | V18 | ○ | V26 | • | C2 | • | P2 | ■ |
|    |   |     |   |     |   |     |   |    |   |    | • |
| V3 | ○ | V11 | • | V19 | • | V27 | • | C3 | ○ | P3 | ■ |
|    |   |     |   |     |   |     |   |    |   |    | • |
| V4 | • | V12 | • | V20 | ○ | V28 | ○ | C4 | • | P4 | ■ |

TABLE 6-continued

Mononuclear Cell Harvesting Stage
(PRP Flush Phase)

| V5 | • | V13 | ○ | V21 | ○ | V29 | • | P5 | ■ |
|    |   |     |   |     |   |     |   |    | • |
| V6 | ○ | V14 | ○ | V22 | • | V30 | • | P6 | ▶ |
| V7 | ○ | V15 | • | V23 | ○ |     |   |    |   |
| V8 | ○ | V16 | ○ | V24 | ○ |     |   |    |   |

Where:
• indicates a tubing occluded or closed condition.
○ indicates a tubing non-occluded or opened condition.

▶ indicates a pump on condition, during which the pump rotors rotate and engage the pump tubing to convey fluid in a peristaltic fashion.

■ ○ indicates an opened, pump off condition, during which the pump rotors are not rotating and in which the pump rotors do not engage the pump tubing loop, and therefore permit fluid flow through the pump tubing loop.

■ • indicates a closed, pump off condition, during which the pump rotors are not rotating, and in which the pump rotors do engage with pump tubing loop, and therefore do not permit fluid flow through the pump tubing loop.

During the PRP flush stage 242, the controller 222 configures the pump stations PSL, PSM, and PSR to stop whole blood recirculation, and, while continuing rotation of the compartment 38, to pump $VOL_{PRP}$ to the processing compartment 38 through tubing T11. $VOL_{PRP}$ is conveyed by the pump P6 through tubing T12 into the right cassette 23R, and thence to tubing T11, for entry into the processing compartment 38 through tubing T4 and port 48. PRBC are conveyed from the processing compartment 38 through port 50 and tubing T5 into the middle cassette 23M, and thence into tubings T8 and T7 into the left cassette 23L. The PRBC is conveyed into tubing T9 for return to the donor/patient. No other fluid is conveyed in the fluid circuit 15 during this phase 242.

The return of $VOL_{PRP}$ restores the volume of liquid in container PPP to $VOL_{SUS}$, as collected during the preliminary processing cycle 228 previously described. The return of $VOL_{PRP}$ also preserves a low platelet population in the $VOL_{SUS}$ in the container PPP slated for suspension of MNC. The return of $VOL_{PRP}$ also conveys residual MNC present in the first transition region 116 before $TC_1=T_1$ (and therefore not part of $VOL_{MNC}$), back to the processing compartment 38 for further collection in a subsequent main processing cycle 230.

(iii) Third Phase (MNC Suspension)

With the return of $VOL_{PRP}$ to the compartment 38, the controller 222 enters the MNC suspension phase 244 of the MNC harvesting stage 234. During this phase 244, a portion of the $VOL_{SUS}$ in the container PPP is conveyed with $VOL_{MNC}$ into the container MNC.

The configuration of the fluid circuit 200 during the MNC suspension phase 244 is shown in FIG. 26, and is further summarized in Table 7.

TABLE 7

Mononuclear Cell Harvesting Stage
(MNC Suspension Phase)

| V1 | • | V9  | • | V17 | ○ | V25 | ○ | C1 | • | P1 | ■ |
|    |   |     |   |     |   |     |   |    |   |    | ○ |
| V2 | • | V10 | ○ | V18 | ○ | V26 | • | C2 | • | P2 | ■ |
|    |   |     |   |     |   |     |   |    |   |    | • |
| V3 | ○ | V11 | • | V19 | • | V27 | • | C3 | • | P3 | ■ |
|    |   |     |   |     |   |     |   |    |   |    | • |
| V4 | • | V12 | • | V20 | ○ | V28 | • | C4 | • | P4 | ■ |
|    |   |     |   |     |   |     |   |    |   |    | • |

TABLE 7-continued

Mononuclear Cell Harvesting Stage
(MNC Suspension Phase)

| V5 | • | V13 | o | V21 | o | V29 | o |    | P5 | ■• |
| V6 | o | V14 | o | V22 | • | V30 | • |    | P6 | ▶ |
| V7 | o | V15 | • | V23 | o |     |   |    |    |   |
| V8 | o | V16 | o | V24 | o |     |   |    |    |   |

Where:
• indicates a tubing occluded or closed condition.
o indicates a tubing non-occluded or opened condition.
▶ indicates a pump on condition, during which the pump rotors rotate and engage the pump tubing to convey fluid in a peristaltic fashion.
■ o indicates an opened, pump off condition, during which the pump rotors are not rotating and in which the pump rotors do not engage the pump tubing loop, and therefore permit fluid flow through the pump tubing loop.
■ • indicates a closed, pump off condition, during which the pump rotors are not rotating, and in which the pump rotors do engage with pump tubing loop, and therefore do not permit fluid flow through the pump tubing loop.

In the MNC suspension phase 244, the controller closes C3 to stop the return to PRBC to the donor/patient. A predetermined aliquot of $VOL_{SUS}$ (e.g., 5 ml to 10 ml) is conveyed by the pump P6 through tubing T12 into the right cassette 23R and then into tubing T13. As FIG. 26 shows, the aliquot of $VOL_{SUS}$ further advances $VOL_{MNC}$ through the tubing T13 into the container MNC.

(iii) Fourth Phase (Clean Up)

At this time, the controller 222 enters the final, clean up phase 246 of the MNC harvesting stage 234. During this phase 246, the controller 222 returns PRBC resident in the tubing T10 to the processing compartment 38.

The configuration of the fluid circuit 200 during the clean up phase 246 is shown in FIG. 27, and is further summarized in Table 7.

TABLE 7

Mononuclear Cell Harvesting Stage
(Clean Up Phase)

| V1 | • | V9  | • | V17 | • | V25 | • | C1 | • | P1 | ■• |
| V2 | • | V10 | • | V18 | • | V26 | • | C2 | • | P2 | ■• |
| V3 | • | V11 | • | V19 | • | V27 | o | C3 | • | P3 | ■• |
| V4 | • | V12 | • | V20 | • | V28 | o | C4 | • | P4 | ■• |
| V5 | • | V13 | • | V21 | o | V29 | • |    |   | P5 | ■• |
| V6 | • | V14 | • | V22 | • | V30 | o |    |   | P6 | ▶ |
| V7 | • | V15 | • | V23 | o |     |   |    |   |    |   |
| V8 | • | V16 | • | V24 | • |     |   |    |   |    |   |

Where:
• indicates a tubing occluded or closed condition.
o indicates a tubing non-occluded or opened condition.
▶ indicates a pump on condition, during which the pump rotors rotate and engage the pump tubing to convey fluid in a peristaltic fashion.
■ o indicates an opened, pump off condition, during which the pump rotors are not rotating and in which the pump rotors do not engage the pump tubing loop, and therefore permit fluid flow through the pump tubing loop.
■ • indicates a closed, pump off condition, during which the pump rotors are not rotating, and in which the pump rotors do engage with pump tubing loop, and therefore do not permit fluid flow through the pump tubing loop.

The clean up phase 246 returns any residual MNC present in the second transition region 118 (see FIG. 28) after $TC_2=T_2$ (and therefore not part of $VOL_{SEN}$), back to the processing compartment 38 for further collection in a subsequent processing cycle.

In the clean up phase 246, the controller 222 closes all valve stations in the left and middle cassettes 23L and 23M and configures the right pump station PSR to circulated PRBC from tubing T10 back into the processing compartment 38 through tubings T11 and T4. During this period, no components are being drawn from or returned to the donor/patient.

At the end of the clean up phase 246, the controller 222 commences a new main processing cycle 230. The controller 222 repeats a series of main processing cycles 230 until the desired volume of MNC targeted for the entire procedure is reached.

At the end of the last main processing cycle 230, the operator may desire additional $VOL_{SUS}$ to further dilute the MNC collected during the procedure. In this circumstance, the controller 222 can be commanded to configure the fluid circuit 200 to carry out a preliminary processing cycle 228, as above described, to collect additional $VOL_{SUS}$ in the container PPP. The controller 222 then configures the fluid circuit 200 to carry out an MNC suspension phase 244, to convey additional $VOL_{SUS}$ into the container MNC to achieve the desired dilution of $VOL_{MNC}$.

IV. Alternative Mononuclear Cell Processing Procedure

FIG. 29 shows an alternative embodiment of a fluid circuit 300, which is suited for collecting and harvesting MNC. The circuit 300 is in most respects the same as the circuit 200, shown in FIG. 6, and common components are given the same reference numbers.

The circuit 300 differs from the circuit 200 in that the second compartment 310 of the container 14 is identical to the compartment 38, and thereby itself comprises a second blood processing compartment with the same features as compartment 38. The compartment 310 includes interior seals, as shown for compartment 38 in FIG. 4, creating the same blood collection regions for PRP and PRBC, the details of which are not shown in FIG. 29. The compartment 310 includes a port 304 for conveying whole blood into the compartment 310, a port 306 for conveying PRP from the compartment 310, and a port 302 for conveying PRBC from the compartment 310. Compartment 310 also includes a tapered ramp 84, as shown in FIGS. 16A and 16B and as earlier described in connection with the compartment 38.

The fluid circuit 300 also differs from the fluid circuit 200 in that tubings T14, T18, and T19 are not included. In addition, the container PRBC is not included. Instead, fluid circuit 300 includes several new tubing paths and clamps, as follows:

Tubing path T21 leads from the PRP outlet port 306 of the compartment 310 through a new clamp C5 to join tubing path T10.

Tubing path T22 leads from the WB inlet port 306 of the compartment 310 through a new air detector D3 and a new clamp C6 to join tubing path T3.

Tubing path T33 leads from the PRBC outlet port 302 of the compartment 310 through a new clamp C8 to join tubing T4.

New clamp C7 is also provided in tubing T3 upstream of the air detector D1.

New clamp C9 is also provided in tubing T10 between the optical sensor OS and the junction of new tubing T21.

Using circuit 300, the controller 222 proceeds through the previous described priming cycle 226, preliminary processing cycle 228, and main processing cycle 230 as previously described for circuit 200, up through the MNC accumulation phase 236. The PRBC collect phase 238 differs when using the circuit 300, in that PRBC used for subsequent removal of MNC from the compartment 38 are processed and collected in the second compartment 310.

More particularly, as shown in FIG. 30, during the PRBC collection phase 238, the controller 222 conveys a volume of whole blood from the donor/patient into the second compartment 310. The whole blood volume is drawn by pump P2 through tubing T1 into tubing T3 and thence through open clamp C6 into tubing T22, which leads to the compartment 310. Clamp C7 is closed, to block conveyance of whole blood into the compartment 38, where the MNC have been accumulated for harvesting. Clamp C9 is also closed to block conveyance of PRP from the compartment 38, thereby keeping the accumulation of MNC undisturbed in the compartment 38.

In the compartment 310, the whole blood volume is separated into PRBC and PRP, in the same fashion that these components are separated in the compartment 38. PRP is conveyed from the compartment 310 through tubing T23 and open clamp C5 by operation of the pump P5, for return to the donor/patient. The clamp C8 is closed, to retain PRBC in the compartment 310.

The controller 222 also conducts a different MNC removal phase 240 using circuit 300. As shown in FIG. 31, during the MNC removal phase 240, the controller 222 recirculates a portion of the drawn whole blood back to the donor/patient, while directing another portion of the whole blood into the compartment 310, following the same path as previously described in connection with FIG. 30. The controller 222 opens clamps C8 and C9, while closing clamp C5. The whole blood entering the compartment 310 displaces PRBC through the PRBC outlet port 302 into tubing T23. The PRBC from the compartment 310 enters the WB inlet port 48 of the compartment 38. As before described, the incoming flow of PRBC from outside the compartment 38 increases the hematocrit of PRBC within the compartment 38, causing the accumulated MNC to float to the interface 58. As before described, the incoming PRBC from outside the compartment 38 displaces PRP through the PRP port 46, together with the MNC Region, shown in FIG. 31. This MNC Region is detected by the optical sensor OS and harvested in subsequent processing 242, 244, and 246 in the same fashion as described for circuit 200.

Various features of the inventions are set forth in the following claims.

We claim:

1. A blood processing system comprising
   a processing chamber having a single fluid flow access, the processing chamber containing residual air,
   tubing communicating with the single access,
   a pump element in the tubing, and
   a controller coupled to the pump element operative in a first mode to operate the pump element to draw a vacuum in the processing chamber to remove the residual air without introducing liquid into the processing chamber, the pump element being operative in a second mode to open communication between the tubing and a source of liquid after removal of the residual air and while the vacuum exists in the processing chamber, whereby the vacuum draws the liquid into the processing chamber to prime the processing chamber, and whereby the residual air is vented from the processing chamber prior to use.

2. A blood processing system according to claim 1 wherein, during the second mode, the controller commands the pump element to convey the liquid into the processing chamber while the vacuum also draws the liquid into the processing chamber.

3. A method of priming a container having a single fluid flow access, the container containing residual air, the method comprising the steps of
   (i) coupling the single access to tubing which includes a pump element,
   (ii) operating the pump element to draw a vacuum in the container and thereby remove the residual air from the container through the single access without introducing liquid into the container, and
   (iii) after step (ii), opening communication between the tubing and a source of liquid while the vacuum exists in the container, whereby the vacuum draws the liquid into the container through the single access and thereby primes the container.

4. A method according to claim 3 wherein step (iii) includes operating the pump element to convey the liquid into the container through the single access while the vacuum also draws the liquid into the container through the single access.

* * * * *

UNITED STATES PATENT AND TRADEMARK OFFICE
CERTIFICATE OF CORRECTION

PATENT NO. : 6,027,441
DATED : February 22, 2000
INVENTOR(S) : Robert J. Cantu, Kyungyoon Min and Douglas W. Reitz It is certified that error appears in the above-identified patent and that said Letters Patent is hereby corrected as shown below:

Column 5,
Line 63, Table 1, delete "V53" and substitute -- VS3 --

Column 6,
Line 21, delete "that 20 the" and substitute -- that the --

Column 8,
Line 37, delete "28. The" and substitue -- 28, the --

Column 9,
Line 17, delete "angle a" and substitue -- angle α --

Column 11,
Line 44, after "Cycle" insert a paragraph break.

Column 14,
Line 52, delete "H." and substitute -- $H_O$ --

Column 15,
Line 54, delete "95 × $10_{-9}$ s" and substitute -- 95 × $10^{-9}$ s --

Column 19,
Line 25, delete "Autopheresis-Cs®" and substitute -- Autopheresis –C® --

Signed and Sealed this

Twenty-ninth Day of June, 2004

JON W. DUDAS
*Acting Director of the United States Patent and Trademark Office*